(12) United States Patent
Kim et al.

(10) Patent No.: US 9,370,530 B2
(45) Date of Patent: *Jun. 21, 2016

(54) COMBINATION, KIT AND METHOD OF REDUCING INTRAOCULAR PRESSURE

(71) Applicant: Inotek Pharmaceuticals Corporation, Lexington, MA (US)

(72) Inventors: Norman N. Kim, Westford, MA (US); William K. McVicar, Sudbury, MA (US); Thomas G. McCauley, Cambridge, MA (US); Rudolf A. Baumgartner, Sudbury, MA (US)

(73) Assignee: Inotek Pharmaceuticals Corporation, Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/517,509

(22) Filed: Oct. 17, 2014

(65) Prior Publication Data

US 2015/0038448 A1 Feb. 5, 2015

Related U.S. Application Data

(63) Continuation of application No. 13/004,380, filed on Jan. 11, 2011, now Pat. No. 8,877,732.

(60) Provisional application No. 61/293,806, filed on Jan. 11, 2010.

(51) Int. Cl.
| | |
|---|---|
| A61K 31/70 | (2006.01) |
| A61K 31/7076 | (2006.01) |
| A61K 9/00 | (2006.01) |
| A61K 31/165 | (2006.01) |
| A61K 31/19 | (2006.01) |
| A61K 31/216 | (2006.01) |
| A61K 45/06 | (2006.01) |
| C07H 19/16 | (2006.01) |

(52) U.S. Cl.
CPC ........... *A61K 31/7076* (2013.01); *A61K 9/0048* (2013.01); *A61K 31/165* (2013.01); *A61K 31/19* (2013.01); *A61K 31/216* (2013.01); *A61K 45/06* (2013.01); *C07H 19/16* (2013.01)

(58) Field of Classification Search
CPC ............ A61K 31/7076; A61K 31/216; A61K 9/0048; A61K 31/165; A61K 45/06; A61K 31/19; C07H 19/16
See application file for complete search history.

(56) References Cited

U.S. PATENT DOCUMENTS

| | | | |
|---|---|---|---|
| 3,819,613 A | 6/1974 | Kawazoe et al. | |
| 3,832,341 A | 8/1974 | Duschinsky | |
| 4,242,505 A | 12/1980 | Kawahara et al. | |
| 4,849,311 A | 7/1989 | Itoh et al. | |
| 4,968,697 A | 11/1990 | Hutchison | |
| 5,140,015 A | 8/1992 | Olsson et al. | |
| 5,206,222 A | 4/1993 | Forman et al. | |
| 5,219,840 A | 6/1993 | Gadient et al. | |
| 5,221,763 A * | 6/1993 | Ueno et al. | 560/121 |
| 5,278,150 A | 1/1994 | Olsson et al. | |
| 5,280,015 A | 1/1994 | Jacobson et al. | |
| 5,296,504 A | 3/1994 | Stjernschantz et al. | |
| 5,304,277 A | 4/1994 | Ohara et al. | |
| 5,338,430 A | 8/1994 | Parsonage et al. | |
| 5,407,793 A | 4/1995 | Del Nido et al. | |

(Continued)

FOREIGN PATENT DOCUMENTS

| | | |
|---|---|---|
| CN | 1164122 A | 11/1997 |
| CN | 101010085 A | 8/2007 |

(Continued)

OTHER PUBLICATIONS

M. J. O'Neil et al. (eds.), "The Merck Index, 14th Edition," Merck & Co., Whitehouse Station, NJ, 2006, only pp. 1693 supplied (see "Unoprostone").*
Stewart, William C. et al., "Beta-Blocker-Induced Complications and the Patient With Glaucoma," Archives of Internal Medicine, vol. 158(3):221-226 (1998).
Stewart, William C., "Perspectives in the medical treatment of glaucoma," Current Opinion in Ophthalmology, vol. 10:99-108 (1999).
Sugrue, Michael F., "Pharmacological and Ocular Hypotensive Properties of Topical Carbonic Anhydrase Inhibitors," Progress in Retinal and Eye Research, vol. 19(1):87-112 (2000).
Supplementary European Search Report for Application No. 11732309.7, 10 pages, dated Jul. 31, 2013.
Thompson, Robert D. et al., "Activity of N6-Substituted 2-Chloroadenosines at A1 and A2 Adenosine Receptors," J. Med. Chem., vol. 34:3388-3390 (1991).

(Continued)

*Primary Examiner* — Lawrence E Crane
(74) *Attorney, Agent, or Firm* — Nelson Mullins Riley & Scarborough LLP; Jane E. Remillard, Esq.; Cynthia L. Kanik

(57) ABSTRACT

The present invention is directed to a composition or a kit comprising a combination of a prostaglandin analog and an adenosine receptor $A_1$ agonist and to a method of reducing intraocular pressure (IOP) in a subject using such combination or kit. In some embodiments, the adenosine receptor $A_1$ agonist is Compound A, ((2R,3S,4R,5R)-5-(6-(cyclopentylamino)-9H-purin-9-yl)-3,4-dihydroxytetrahydrofuran-2-yl) methyl nitrate, having the structure,

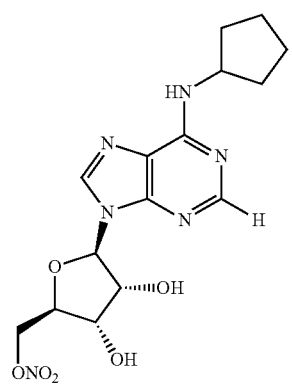

25 Claims, 6 Drawing Sheets

(56) References Cited

U.S. PATENT DOCUMENTS

| | | |
|---|---|---|
| 5,422,368 A | 6/1995 | Stjernschantz et al. |
| 5,443,836 A | 8/1995 | Downey et al. |
| 5,589,467 A | 12/1996 | Lau et al. |
| 5,591,887 A * | 1/1997 | Ueno et al. ............... 560/121 |
| 5,604,210 A | 2/1997 | Nagaoka et al. |
| 5,620,676 A | 4/1997 | Jacobson et al. |
| 5,770,759 A * | 6/1998 | Ueno et al. ............... 560/53 |
| 5,789,416 A | 8/1998 | Lum et al. |
| 5,801,159 A | 9/1998 | Miller et al. |
| 6,180,615 B1 | 1/2001 | Zablocki et al. |
| 6,214,807 B1 | 4/2001 | Zablocki et al. |
| 6,326,359 B1 | 12/2001 | Monaghan et al. |
| 6,358,536 B1 | 3/2002 | Thomas |
| 6,368,573 B1 | 4/2002 | Leung |
| 6,403,567 B1 | 6/2002 | Zablocki et al. |
| 6,403,649 B1 * | 6/2002 | Woodward et al. ............ 514/646 |
| 6,407,076 B1 | 6/2002 | Box et al. |
| 6,426,337 B1 | 7/2002 | Cox et al. |
| 6,429,229 B1 | 8/2002 | Bouyssou et al. |
| 6,440,948 B1 | 8/2002 | Zablocki et al. |
| 6,448,236 B1 | 9/2002 | Monaghan et al. |
| 6,525,032 B2 | 2/2003 | Mantell et al. |
| 6,528,494 B2 | 3/2003 | Cox et al. |
| 6,528,516 B1 | 3/2003 | Civan et al. |
| 6,531,457 B2 | 3/2003 | Linden et al. |
| 6,534,486 B1 | 3/2003 | Allen et al. |
| 6,544,960 B1 | 4/2003 | Eldred et al. |
| 6,638,914 B1 | 10/2003 | Fishman et al. |
| 6,753,322 B2 | 6/2004 | Mantell et al. |
| 6,903,079 B2 | 6/2005 | Jagtap et al. |
| 6,921,753 B2 | 7/2005 | Mantell et al. |
| 7,084,127 B2 | 8/2006 | Van Tilburg et al. |
| 7,163,959 B2 | 1/2007 | Stjernschantz et al. |
| 7,189,706 B2 | 3/2007 | Van Tilburg et al. |
| 7,271,157 B2 | 9/2007 | Elzein et al. |
| 7,351,407 B2 | 4/2008 | Fleenor et al. |
| 7,423,144 B2 | 9/2008 | Jagtap et al. |
| 7,713,946 B2 | 5/2010 | Dhalla et al. |
| 7,732,424 B2 * | 6/2010 | Jagtap et al. ............... 514/46 |
| 7,964,191 B2 | 6/2011 | Rodrigues et al. |
| 8,163,737 B2 | 4/2012 | Anderson et al. |
| 8,183,224 B2 | 5/2012 | Jagtap et al. |
| 8,207,215 B2 | 6/2012 | Muller et al. |
| 8,440,639 B2 * | 5/2013 | Kim et al. ............... 514/46 |
| 8,455,457 B2 * | 6/2013 | Kim et al. ............... 514/46 |
| 8,470,800 B2 | 6/2013 | Barman et al. |
| 8,476,247 B2 * | 7/2013 | Kim et al. ............... 514/46 |
| 8,501,708 B2 | 8/2013 | Jagtap |
| 8,609,833 B2 | 12/2013 | Jagtap et al. |
| 8,648,169 B2 | 2/2014 | Saragovi |
| 8,784,886 B2 | 7/2014 | Fawzy et al. |
| 8,877,732 B2 * | 11/2014 | Kim et al. ............... 514/46 |
| 8,895,530 B2 * | 11/2014 | Kim et al. ............... 514/46 |
| 2001/0051612 A1 | 12/2001 | Cristalli |
| 2003/0013675 A1 | 1/2003 | Yeadon et al. |
| 2003/0055021 A1 | 3/2003 | DeNinno et al. |
| 2004/0166168 A1 | 8/2004 | Mathiowitz et al. |
| 2005/0250813 A1 | 11/2005 | Wieckhusen et al. |
| 2006/0009417 A1 | 1/2006 | Elzein et al. |
| 2006/0034941 A1 | 2/2006 | Dobson |
| 2007/0185051 A1 | 8/2007 | Dhalla et al. |
| 2007/0238694 A1 | 10/2007 | Salzman et al. |
| 2008/0050335 A1 | 2/2008 | Faour et al. |
| 2009/0131342 A1 | 5/2009 | Ellis |
| 2009/0220516 A1 | 9/2009 | Laties et al. |
| 2009/0258836 A1 | 10/2009 | Civan et al. |
| 2010/0041552 A1 | 2/2010 | Saxell et al. |
| 2010/0297121 A1 | 11/2010 | Mi |
| 2011/0123622 A1 | 5/2011 | Avery et al. |
| 2011/0172177 A1 | 7/2011 | Kim et al. |
| 2011/0217262 A1 | 9/2011 | Kornfield et al. |
| 2011/0245193 A1 | 10/2011 | Kim et al. |

FOREIGN PATENT DOCUMENTS

| | | |
|---|---|---|
| CN | 101321460 A | 12/2008 |
| DE | 2342479 A1 | 3/1975 |
| EP | 0 364 417 A1 * | 4/1990 |
| FR | 2186470 A1 | 1/1974 |
| GB | 2436255 | 9/2007 |
| JP | 2012-508764 A | 4/2012 |
| KR | 20030005241 A | 1/2003 |
| WO | WO 93/00329 A1 * | 1/1993 |
| WO | 93/23418 A1 | 11/1993 |
| WO | 94/02497 A1 | 2/1994 |
| WO | 95/02604 A1 | 1/1995 |
| WO | 95/11681 A1 | 5/1995 |
| WO | 96/02553 A2 | 2/1996 |
| WO | 97/33590 A1 | 9/1997 |
| WO | 97/33879 A1 | 9/1997 |
| WO | 98/08855 A2 | 3/1998 |
| WO | 98/50047 A1 | 11/1998 |
| WO | 99/20284 A1 | 4/1999 |
| WO | 01/19360 A2 | 3/2001 |
| WO | 01/40245 A1 | 6/2001 |
| WO | 01/45715 A2 | 6/2001 |
| WO | 02/09702 A2 | 2/2002 |
| WO | 02/055085 A2 | 7/2002 |
| WO | 02/083152 A1 | 10/2002 |
| WO | 03/029264 A2 | 4/2003 |
| WO | 03/088978 A1 | 10/2003 |
| WO | 2005/117910 A2 | 12/2005 |
| WO | 2007/064795 A2 | 6/2007 |
| WO | 2008/130520 A1 | 10/2008 |
| WO | 2009/076580 A2 | 6/2009 |
| WO | 2009/100326 A1 | 8/2009 |
| WO | 2010/127210 A1 | 11/2010 |
| WO | 2011/077435 A1 | 6/2011 |

OTHER PUBLICATIONS

Tian, Baohe et al., "Effects of Adenosine Agonists on Intraocular Pressure and Aqueous Humor Dynamics in Cynomolgus Monkeys," Exp. Eye Res., vol. 64:979-989 (1997).

Tsilimbaris, Miltiadis K. et al., "The Use of Atomic Force Microscopy for the Observation of Corneal Epithelium Surface," Invest. Ophthalmol. Vis. Sci., vol. 41:680-686 (2000).

Van Der Wenden, Eleonora M. et al., "5'-Substituted Adenosine Analogs as New High-Affinity Partial Agonists for the Adenosine A1 Receptor," J. Med. Chem., vol. 41:102-108 (1998).

Van Tilburg, Erica W. et al., "2,5'-Disubstituted Adenosine Derivatives: Evaluation of Selectivity and Efficacy for the Adenosine A1, A2A and A3 Receptor," J. Med. Chem., vol. 45:420-429 (2002).

Virág, Lásziό et al., "Effects of poly(ADP-ribose) polymerase inhibition on inflammatory cell migration in a murine model of asthma," Med. Sci. Monit., vol. 10(3):BR77-83 (2004).

Vitrori, Sauro et al., "2-Alkenyl and 2-Alkyl Derivatives of Adenosine and Adenosine-5'-N-Ethyluronamide: Different Affinity and Selectivity of E- and Z-Diastereomers at A2A Adenosine Receptors," J. Med. Chem., vol. 39:4211-4217 (1996).

Vitrori, Sauro et al., "N-Cycloalkyl Derivatives of Adenosine and 1-Deazaadenosine as Agonists and Partial Agonists of the A1 Adenosine Receptor," J. Med. Chem., vol. 43:250-260 (2000).

Viziano, Monica et al., "2-[N'-(3-Arylallylidene)hydrazino]adenosines Showing A2a Adenosine Agonist Properties and Vasodilation Activity," J. Med. Chem., vol. 38:3581-3585 (1995).

Witte, M.B. et al., "Nitric oxide enhances experimental wound healing in diabetes," British Journal of Surgery, vol. 89:1594-1601 (2002).

Woodward, D. et al., "Fixed-Combination and Emerging Glaucoma Therapies," Expert Opinion on Emerging Drugs, 2007, vol. 12, No. 2., pp. 313-327.

Hirao, Mami et al., "Effects of adenosine on optic nerve head circulation in rabbits," Experimental Eye Research, vol. 79:729-735 (2004).

Homma, Hiroshi et al., "Nucleosides and Nucleotides. 112. 2-(1-Hexyn-1-yl)adenosine-5'-uronamides: A New Entry of Selective A2 Adenosine Receptor Agonists with Potent Antihypertensive Activity," J. Med. Chem., vol. 35:2881-2890 (1992).

(56) References Cited

OTHER PUBLICATIONS

Husain, S. et al., "Mechanisms Linking Adenosine A1 Receptors and Extracellular Signal-Regulated Kinase 1/2 Activation in Human Trabecular Meshwork Cells," The Journal of Pharmacology and Experimental Therapeutics, vol. 320(1):258-265 (2007).
Hutchison, Alan J. et al., "2-(Arylalkylamino)adenosin-5'-uronamides: A New Class of Highly Selective Adenosine A2 Receptor Ligands," J. Med. Chem., vol. 33:1919-1924 (1990).
International Search Report and Written Opinion for Application No. PCT/US2011/020808, dated Mar. 30, 2011, pages.
Jacobson, Kenneth A. et al., "Adenosine receptors as therapeutic targets," Nature Reviews Drug Discovery, vol. 5:247-264 (2006).
Jagtap, Prakash G. et al., "2-(N-Acyl) and 2-N-acyl-N6-substituted analogues of adenosine and their affinity at the human adenosine receptors," Bioorganic & Medicinal Chemistry Letters, vol. 14:1495-1498 (2004).
Karl, Mike O. et al., "Differential P1-purinergic modulation of human Schlemm's canal inner-wall cells," Am. J. Physiol. Cell Physiol., vol. 288:C784-C794 (2005).
Kim, N. et al., "INO-8875, An Adenosine A1 Agonist, in Development for Open-Angle Glaucoma Reduces IOP in Three Rabbit Models," Investigative Ophthalmology & Visual Science, vol. 50, E-Abstract 4061 (2009).
Klotz, K.-N. et al., "Comparative pharmacology of human adenosine receptor subtypes—characterization of stably transfected receptors in CHO cells," Naunyn-Schmiedeberg's Arch. Pharmacol., vol. 357:1-9 (1998).
Klotz, Karl-Norbert et al., "Photoaffinity Labeling of A1-adenosine Receptors," The Journal of Biological Chemistry, vol. 260(27):14659-14664 (1985).
Knutsen, Lars J.S. et al., "N-Substituted Adenosines as Novel Neuroprotective A1 Agonists with Dimished Hypotensive Effects," J. Med. Chem., vol. 42:3463-3477 (1999).
Konno, Takashi et al., "2-(1-Hexyn-1-yl)adenosine-induced intraocular hypertension is mediated via K+ channel opening through adenosine A2A receptor in rabbits," European Journal of Pharmacology, vol. 518:203-211 (2005).
Konno, Takashi et al., "Effect of chymase on intraocular pressure in rabbits," European Journal of Pharmacology, vol. 524:132-137 (2005).
Konno, Takashi et al., "Involvement of Adenosine A2a Receptor in Intraocular Pressure Decrease Induced by 2-(1-Octyn-1-yl)adenosine or 2-(6-Cyano-1-hexyn-1-yl)adenosine," J. Pharmacol. Sci., vol. 97:501-509 (2005).
Kristinsson, et al., Herbicidally Active Sulfamoyl Nucleosides: Isolation and Synthesis Synthesis and Chemistry of Agrochemicals IV, published 1995 by American Chemical Society, chapter 19, pp. 206-219.
Kunkel, Steven L. et al., "The role of chemokines in inflammatory joint disease," Journal of Leukocyte Biology, vol. 59:6-12 (1996).
Lesar, Timothy S., "Comparison of ophthalmic beta-blocking agents," Clinical Pharmacy, vol. 6:451-463 (1987).
Lichtenthaler, F.W. et al., "Nucleosides, XVIII. Improved Preparation of Nucleoside 5'-Nitrates," Synthesis, vol. 27:199-201 (1973).
Lohse, Martin J. et al., "8-Cyclopentyl-1,3-dipropylxanthine (DPCPX)—a selective high affinity antagonist radioligand for A1 adenosine receptors," Naunyn-Schmiedeberg's Arch. Pharmacol., vol. 336:204-210 (1987).
Mager, P.P. et al., "Molecular simulation applied to 2-(N'-alkylidenehydrazino)- and 2-(N'-aralkylidenehydrazino) adenosine A2 agonists," Eur. J. Med. Chem., vol. 30:15-25 (1995).
Maillard, Michel C. et al., "Adenosine Receptor Prodrugs: Synthesis and Biological Activity of Derivatives of Potent, A1-Selective Agonists," Journal of Pharmaceutical Sciences, vol. 83(1):46-53 (1994).
Matsuda, Akira et al., "Nucleosides and Nucleotides. 103. 2-Alkynyladenosines: A Novel Class of Selective Adenosine A2 Receptor Agonists with Potent Antihypertensive Effects," J. Med. Chem., vol. 35:241-252 (1992).

McKenzie, Sheila G. et al., "Effects of Adenosine and Related Compounds on Adenylate Cyclase and Cyclic AMP Levels in Smooth Muscle," European Journal of Pharmacology, vol. 41:193-203 (1977).
McWhinney, Charlene D. et al., "Activation of adenosine A3 receptors on macrophages inhibits tumor necrosis factor-a," European Journal of Pharmacology, vol. 310:209-216 (1996).
Mincione, Francesco et al., "The Development of Topically Acting Carbonic Anhydrase Inhibitors as Antiglaucoma Agents," Current Pharmaceutical Design, vol. 14:649-654 (2008).
Missiaen, Ludwig et al., "Effect of adenine nucleosides on myo-inositol-1,4,5-trisphosphate-induced calcium release," Biochem. J., vol. 325:661-666 (1997).
Moos, Walter H. et al., "N6-Cycloalkyladenosines. Potent A1-Selective Adenosine Agonists," Journal of Medicinal Chemistry, vol. 28(10):1383-1384 (1985).
Muller, C.E. et al., "Adenosine Receptor Ligands-Recent Developments Part I. Agonists," Current Medicinal Chemistry, vol. 7:1269-1288 (2000).
Nair, Vasu et al., "Novel, Stable Congeners of the Antiretroviral Compound 2',3'-Dideoxyadenosine," J. Am. Chem. Soc., vol. 111:8502-8504 (1989).
Nell, Peter G. et al., "The Adenosine A1 Receptor and its Ligands," Progress in Medicinal Chemistry, vol. 47:163-201 (2009).
New Zealand Office Action for Application No. 601323, 3 pages, dated Apr. 5, 2013.
Niiya, Kazunori et al., "2-(N'-Alkylidenehydrazino)adenosines: Potent and Selective Coronary Vasodilators," J. Med. Chem., vol. 35:4557-4561 (1992).
Ohno, Michihiro et al., "Modulation of adenosine receptor affinity and intrinsic efficacy in adenine nucleosides substituted at the 2-position," Bioorganic & Medicinal Chemistry, vol. 12:2995-3007 (2004).
Ongini, Ennio et al., "Pharmacology of adenosine A2A receptors," TiPS, vol. 17:364-372 (1996).
Orzalesi, Nicola et al., "Comparison of the Effects of Latanoprost, Travoprost, and Bimatoprost on Circadian Intraocular Pressure in Patients with Glaucoma or Ocular Hypertension," Ophthalmology, vol. 113:239-246 (2006).
Parmely, Michael J. et al., "Adenosine and a Related Carbocyclic Nucleoside Analogue Selectively Inhibit Tumor Necrosis Factor-a Production and Protect Mice against Endotoxin Challenge," The Journal of Immunology, vol. 151 (1):389-396 (1993).
Pitcher, Graham M. et al., "Paw withdrawal threshold in the von Frey hair test is influenced by the surface on which the rat stands," Journal of Neuroscience Methods, vol. 87:185-193 (1999).
Polska, Elzbieta et al., "Effects of Adenosine on Intraocular Pressure, Optic Nerve Head Blood Flow, and Choroidal Blood Flow in Healthy Humans," Investigative Ophthalmology & Visual Science, vol. 44(7):3110-3114 (2003).
Ralevic, Vera et al., "Receptors for Purines and Pyrimidines," Pharmacological Reviews, vol. 50(3):413-492 (1998).
Reinhart, Konrad et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study," Crit. Care Med., vol. 24(5):733-742 (1996).
Reinstein, Leon J. et al., "Suppression of Lipopolysaccharide-stimulated Release of Tumor Necrosis Factor by Adenosine: Evidence for A2 Receptors on Rat Kupffer Cells," Hepatology, vol. 19:1445-1452 (1994).
Riché, Florence et al., "High tumor necrosis factor serum level is associated with increased survival in patients with abdominal septic shock: A prospective study in 59 patients," Surgery, vol. 120(5):801-807 (1996).
Rieger, Jayson M. et al., "Design, Synthesis, and Evaluation of Novel A2A Adenosine Receptor Agonists," J. Med. Chem., vol. 44:531-539 (2001).
Robinson, Ralph P. et al., "Discovery of the Humifumarate and (alpha-L-Alanyloxy)methyl Ether as Prodrugs of an Antirheumatic Oxindole: Prodrugs for the Enolic OH Group," J. Med. Chem., vol. 39:10-18 (1996).

(56) References Cited

OTHER PUBLICATIONS

Roelen, Harlof et al., "N6,C8-Disubstituted Adenosine Derivatives as Partial Agonists for Adenosine A1 Receptors," J. Med. Chem., vol. 39:1463-1471 (1996).
Sajjadi, Fereydoun G. et al., "Inhibition of TNF-a Expression by Adenosine," The Journal of Immunology, vol. 156:3435-3442 (1996).
Schleef, Raymond R. et al., "The Effect of Fibrin on Endothelial Cell Migration in Vitro," Tissue & Cell, vol. 14 (4):629-636 (1982).
Shuman, Dennis A. et al., "The Synthesis of Nucleoside Sulfamates Related to Nucleocidin," Journal of the American Chemical Society, vol. 92(11):3434-3440 (1970).
Soulere, Laurent et al., "Synthesis and Uptake of Nitric Oxide-Releasing Drugs by the P2 Nucleoside Transporter in Trypanosoma equiperdum," Bioorganic & Medicinal Chemistry Letters, vol. 10:1347-1350 (2000).
U.S. Appl. No. 11/137,632, filed May 25, 2005, P. Jagtap.
U.S. Appl. No. 12/221,539, filed Aug. 4, 2008, P. Jagtap.
U.S. Appl. No. 13/451,613, filed Apr. 20, 2012, P. Jagtap.
U.S. Appl. No. 12/771,289, filed Apr. 30, 2010, P. Jagtap.
U.S. Appl. No. 13/004,380, filed Jan. 11, 2011, N. N. Kim.
U.S. Appl. No. 13/051,633, filed Mar. 18, 2011, N. N. Kim.
U.S. Appl. No. 13/051,655, filed Mar. 18, 2011, N. N. Kim.
U.S. Appl. No. 13/071,993, filed Mar. 25, 2011, P. Jagtap.
U.S. Appl. No. 13/072,349, filed Mar. 25, 2011, N. N. Kim.
U.S. Appl. No. 13/909,288, filed Jun. 4, 2013, N. N. Kim.
U.S. Appl. No. 14/552,160, filed Nov. 2, 2014, N. N. Kim.
U.S. Appl. No. 13/750,389, filed Jan. 25, 2013, W. McVicar.
U.S. Appl. No. 14/211,516, filed Mar. 14, 2014, W. McVicar.
U.S. Appl. No. 14/211,567, filed Mar. 14, 2014, W. McVicar.
U.S. Appl. No. 11/137,632, Jun. 23, 2008.
U.S. Appl. No. 11/137,632, Nov. 8, 2007.
U.S. Appl. No. 11/137,632, May 9, 2007.
U.S. Appl. No. 12/221,539, Jan. 23, 2012.
U.S. Appl. No. 12/221,539, Sep. 2, 2011.
U.S. Appl. No. 12/221,539, Apr. 28, 2011.
U.S. Appl. No. 12/221,539, Sep. 22, 2010.
U.S. Appl. No. 13/451,613, Aug. 15, 2013.
U.S. Appl. No. 13/451,613, Dec. 17, 2012.
U.S. Appl. No. 12/771,289, May 16, 2013.
U.S. Appl. No. 12/771,289, Jan. 3, 2013.
U.S. Appl. No. 12/771,289, May 23, 2012.
U.S. Appl. No. 13/004,380, Jun. 24, 2014.
U.S. Appl. No. 13/004,380, Mar. 14, 2013.
U.S. Appl. No. 13/004,380, Sep. 10, 2013.
U.S. Appl. No. 13/051,633, Jan. 14, 2013.
U.S. Appl. No. 13/051,633, May 17, 2012.
U.S. Appl. No. 13/051,655, Feb. 4, 2013.
U.S. Appl. No. 13/051,655, May 16, 2012.
U.S. Appl. No. 13/071,993, Apr. 3, 2013.
U.S. Appl. No. 13/071,993, Jan. 8, 2013.
U.S. Appl. No. 13/071,993, Jun. 13, 2012.
U.S. Appl. No. 13/072,349, Mar. 4, 2013.
U.S. Appl. No. 13/072,349, Mar. 27, 2012.
U.S. Appl. No. 13/909,288, Jul. 24, 2014.
U.S. Appl. No. 13/909,288, Jan. 2, 2014.
U.S. Appl. No. 13/750,389, May 21, 2015.
U.S. Appl. No. 13/750,389, Sep. 23, 2014.
U.S. Appl. No. 14/211,567, May 13, 2015.
Accession No. 1994:153455, Higuchi, T. et al., "Evaluation of Serum Lactate-Dehydrogenase Activity for Estimation of Energy-Expenditure in Human-Subjects," Ergonomics, vol. 37(3):389-397 (1994).
Accession No. 2001:494425, Martin, H. et al., "The Guardian/Observer: Information developments since 1998," Aslib Proceedings, vol. 53(5):161-166 (2001).
Accession No. 2002:660483, Shore, G.M. et al., "eta '(eta)->gamma gamma: A tale of two anomalies," Physica Scripta, vol. T99:84-95 (2002).
Accession No. 2004:827690, Tacke, R. et al., "Sila-haloperidol: a silicon analogue of the dopamine (D-2) receptor antagonist haloperidol," Organometallics, vol. 23(19):4468-4477 (2004).
ACS Registry No. 151563-23-4 (1993).
ACS Registry No. 365533-72-8 (2001).
ACS Registry No. 365533-73-9 (2001).
ACS Registry No. 365533-74-0 (2001).
Al-Mughales, J. et al., "The chemoattractant activity of rheumatoid synovial fluid for human lymphocytes is due to multiple cytokines," Clin. Exp. Immunol., vol. 106:230-236 (1996).
Appel, S. et al., "Modelling of the pharmacodynamic interaction of an A1 adenosine receptor agonist and antagonist in vivo: N6-cyclopentyladenosine and 8-cyclopentyltheophylline," British Journal of Pharmacology, vol. 115:1253-1259 (1995).
Avila, M et al. British Journal of Pharmacology,"A1-, A2a-, and A3-subtype adenosine receptors modulate intraocular pressure in the mouse," 2001, vol. 134, pp. 241-245.
Baraldi, Pier Giovanni et al., "Synthesis and Biological Activity of a New Series of N6-Arylcarbamoyl, 2-(Ar)alkynyl-N6-arylcarbamoyl, and N6-Carboxamido Derivatives of Adenosine-5'-N-ethyluronamide as A1 and A3 Adenosine Receptor Agonists," J. Med. Chem., vol. 41:3174-3185 (1998).
Bell, Jerald, A. et al., "Ocular Hypertension," eMedicine Ophthalmology, retreived online at: http://emedicine.medscape.com/article/1207470-overview (2008).
Beukers et al., "New, Non-Adenosine, High-Potency Agonists for the Human Adenosine A2B Receptor with an Improved Selectivity Profile Compared to the Reference Agonist N-Ethylcarboxamidoadenosine" J. Med. Chem., 2004, vol. 47, pp. 3707-3709.
Bouma, Maarten G. et al., "Differential Regulatory Effects of Adenosine on Cytokine Release by Activated Human Monocytes," The Journal of Immunology, vol. 153:4159-4168 (1994).
Bradley et al., "Purine Nucleoside-Dependent Inhibition of Cellular Proliferation in 1321N1 Human Astrocytoma Cells." J. Pharmacol. Expt. Ther., 2001, vol. 299, pp. 748-752.
Broadley, Kenneth J. et al., "Drugs modulating adenosine receptors as potential therapeutic agents for cardiovascular diseases," Exp. Opin. Ther. Patents, vol. 10(11):1669-1692 (2000).
Brooks, Anne M.V. et al., "Ocular beta-Blockers in Glaucoma Management, Clinical Pharmacological Aspects," Drugs & Aging, vol. 2(3):208-221 (1992).
Bruns, Robert F. et al., "Characterization of the A2 Adenosine Receptor Labeled by [3H]NECA in Rat Striatal Membranes," Biological Pharmacology, vol. 89:331-346 (1986).
Bruns, Robert F., "Adenosine receptor activation in human fibroblasts: nucleoside agonists and antagonists," Can. J. Physiol. Pharmacol., vol. 58:673-691 (1980).
Camaioni, Emidio et al., "Adenosine Receptor Agonists: Synthesis and Biological Evaluation of the Diastereoisomers of 2-(3-Hydroxy-3-phenyl-1-propyn-1-yl)NECA," Bioorganic & Medicinal Chemistry, vol. 5(12):2267-2275 (1997).
Chinese Office Action for Application No. 201080018539.X, 9 pages, dated Nov. 2, 2012.
Cristalli, Gloria et al., "2-Alkynyl Derivatives of Adenosine and Adenosine-5'-N-ethyluronamide as Selective Agonists at A2 Adenosine Receptors," J. Med. Chem., vol. 35:2363-2368 (1991).
Cristalli, Gloria et al., "2-Alkynyl Derivatives of Adenosine-5'-N-ethyluronamide: Selective A2 Adenosine Receptor Agonists with Potent Inhibitory Activity on Platelet Aggregation," J. Med. Chem., vol. 37:1720-1726 (1994).
Cristalli, Gloria et al., "2-Aralkynyl and 2-Heteroalkynyl Derivatives of Adenosine-5'-N-ethyluronamide as Selective A2a Adenosine Receptor Agonists," J. Med. Chem., vol. 38:1462-1472 (1995).
Crosson, Craig E. et al., "Characterization of Ocular Hypertension Induced by Adenosine Agonists," Investigative Ophthalmology & Visual Science, vol. 37(9):1833-1839 (1996).
Crosson, Craig E. et al., "Modulation of Conventional Outflow Facility by the Adenosine A1 Agonist N6-Cyclohexyladenosine," Investigative Ophthalmology & Visual Science, vol. 46(10):3795-3799 (2005).

(56) References Cited

OTHER PUBLICATIONS

Crosson, Craig E. et al., "Modulation of Intraocular Pressure by Adenosine Agonists," Journal of Ocular Pharmacology, vol. 10(1):379-383 (1994).
Crosson, Craig E. et al., "Ocular effects associated with the chronic administration of the adenosine A1 agonist cyclohexyladenosine," Current Eye Research, vol. 21(4):808-813 (2000).
Crosson, Craig E., "Adenosine Receptor Activation Modulates Intraocular Pressure in Rabbits," The Journal of Pharmacology and Experimental Therapeutics, vol. 273(1):320-326 (1995).
Crosson, Craig E., "Intraocular Pressure Responses to the Adenosine Agonist Cyclohexyladenosine: Evidence for a Dual Mechanism of Action," Investigative Ophthalmology & Visual Science, vol. 42(8):1837-1840 (2001).
Crosson, Craig E., "Ocular hypotensive activity of the adenosine agonist (R)-phenylisopropyladenosine in rabbits," Current Eye Research, vol. 11(5):453-458 (1992).
Daines, Bradley S. et al., "Intraocular Adenosine Levels in Normal and Ocular-Hypertensive Patients," Journal of Ocular Pharmacology and Therapeutics, vol. 19(2):113-119 (2003).
Dalpiaz, Alessandro et al., "Development and characterization of biodegradable nanospheres as delivery systems of anti-ischemic adenosine derivatives," Biomaterials, vol. 26:1299-1306 (2005).
Dalpiaz, Alessandro et al., "Fabrication Via a Nonaqueous Nanoprecipitation Method, Characterization and In Vitro Biological Behavior of N6-Cyclopentyladenosine-Loaded Nanoparticles," Journal of Pharmaceutical Sciences, vol. 98 (11):4272-4284 (2009).
Dalpiaz, Alessandro et al., "Synthesis and Study of 5'-Ester Prodrugs of N6-Cyclopentyladenosine, a Selective A1 Receptor Agonist," Pharmaceutical Research, vol. 18(4):531-536 (2001).
De Lean, Andre et al., "Validation and Statistical Analysis of a Computer Modeling Method for Quantitative Analysis of Radioligand Binding Data for Mixtures of Pharmacological Receptor Subtypes," Molecular Pharmacology, vol. 21:5-16 (1982).
Deninno, Michael P. et al., "3'-Aminoadenosine-5'-uronamides: Discovery of the First Highly Selective Agonist at the Human Adenosine A3 Receptor," J. Med. Chem., vol. 46:353-355 (2003).
Elzein, Elfatih et al., "A1 adenosine receptor agonists and their potential therapeutic applications," Expert Opinion on Investigational Drugs, vol. 17(12):1901-1910 (2008).
Epple et al., "Solid-Phase Synthesis of Nucleoside Analogues" Journal of Combinatorial Chemistry (2003) vol. 5 pp. 292-310.
Fisher, Charles J. Jr. et al., "Treatment of Septic Shock with the Tumor Necrosis Factor Receptor : Fc Fusion Protein," N. Engl. J. Med., vol. 334(26):1697-1702 (1996).
Fleischhauer, J.C. et al., "Common Actions of Adenosine Receptor Agonists in Modulating Human Trabecular Meshwork Cell Transport," J. Membrane Biol., vol. 193:121-136 (2003).
Fleisher, David et al., "Improved oral drug delivery: solubility limitations overcome by the use of prodrugs," Advanced Drug Delivery Reviews, vol. 19:115-130 (1996).
Follmann, Hartmut et al., "Adenine Nucleosides in Solution: Circular Dichroism Studies and Base Conformation," Eur. J. Biochem., vol. 58:31-41 (1975).
Francis, John E. et al., "Highly Selective Adenosine A2 Receptor Agonists in a Series of N-Alkylated 2-Aminoadenosines," J. Med. Chem., vol. 34:2570-2579 (1991).
Fredholm, Berth B. et al., "International Union of Pharmacology. XXV. Nomenclature and Classification of Adenosine Receptors," Pharmacological Reviews, vol. 53(4):527-552 (2001).
Frishman, William H. et al., "Topical Ophthalmic Beta-Adrenergic Blockade for the Treatment of Glaucoma and Ocular Hypertension," J. Clin. Pharmacol., vol. 34:795-803 (1994).
Gandolfi, Stefano et al., "Three-Month Comparison of Bimatoprost and Latanoprost in Patients With Glaucoma and Ocular Hypertension," Advances in Therapy, vol. 18(3):110-121 (2001).
Gurwood, Andrew S., "Comparing selective laser trabeculoplasty witih Latanoprost for the control of intraocular pressure," Br. J. Ophthalmol. vol. 89(11):1413-1417 (2005).
Haskó, György et al., "Adenosine Receptor Agonists Differentially Regulate IL-10, TNF-a, and Nitric Oxide Production in RAW 264.7 Macrophages and in Endotoxemic Mice," The Journal of Immunology, vol. 157:4634-4640 (1996).

* cited by examiner

Mean IOP Measured Over Several Days Following Repeated Ocular Administration of Latanoprost Alone or in Combination with Compound A in Normotensive Monkeys Mean Percent Change from Baseline in IOP Measured Over Several Days Following Repeated Ocular Administration of Latanoprost Alone or in Combination with Compound A in Normotensive Monkeys

COMBINATION, KIT AND METHOD OF REDUCING INTRAOCULAR PRESSURE

RELATED APPLICATIONS

This application is a continuation of U.S. application Ser. No. 13/004,380 filed Jan. 11, 2011, now issued as U.S. Pat. No. 8,877,732, which claims priority to U.S. Provisional Application No. 61/293,806, filed Jan. 11, 2010. The contents of any patents, patent applications, and references cited throughout this specification are hereby incorporated by reference in their entireties.

TECHNICAL FIELD OF THE INVENTION

The present invention is directed to a combination or a kit comprising a prostaglandin analog and an adenosine receptor $A_1$ agonist, and to a method of reducing intraocular pressure (IOP) in a subject using such combination or kit. In one embodiment, the invention is directed to a combination of latanoprost marketed under the brand Xalatan™ and Compound A.

Latanoprost is a prostaglandin $F_{2\alpha}$ analogue. Its chemical name is isopropyl-(Z)-7[(1R,2R,3R,5S)3,5-dihydroxy-2-[(3R)-3-hydroxy-5-phenylpentyl]cyclopentyl]-5-heptenoate and has the following chemical structure:

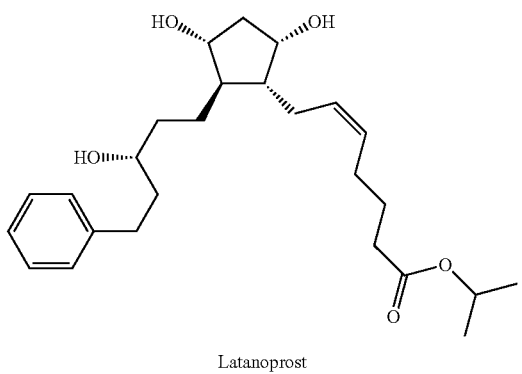 [SMILES: CC(C)OC(=O)CCC/C=C\C[C@@H]1[C@@H](CC[C@@H](O)CCc2ccccc2)[C@H](O)C[C@@H]1O]

Latanoprost

Compound A is an adenosine receptor $A_1$ agonist and has the following structure:

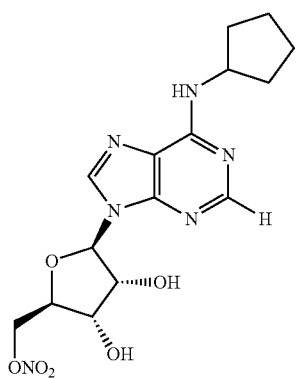

((2R,3S,4R,5R)-5-(6-(cyclopentylamino)-9H-purin-9-yl)-3,4-dihydroxytetrahydrofuran-2-yl)methyl nitrate.

BACKGROUND OF THE INVENTION

Glaucoma refers to a group of optic neuropathies that are characterized by loss of retinal ganglion cells and atrophy of the optic nerve with resultant visual field loss. The disease is the leading cause of irreversible blindness worldwide and the second leading cause of blindness, behind cataracts. Clinical trials have demonstrated that elevated IOP is a major risk factor for glaucoma and have validated the role of lowering IOP in the management of glaucoma.

Glaucoma is classified according to three parameters: 1) the underlying cause, i.e., primary (idiopathic) or secondary (associated with some other ocular or systemic conditions); 2) the state of the anterior chamber angle, i.e., open angle (open access of the outflowing aqueous humor to trabecular meshwork) or closed angle (narrow angle; the trabecular meshwork is blocked by apposition of the peripheral iris and the cornea); and 3) chronicity, i.e., acute or chronic. Although secondary forms of glaucoma with clear etiologies do exist (e.g., pseudoexfoliation and pigmentary dispersion), the most common form of glaucoma is primary open angle glaucoma (POAG).

Occular Hypertension (OHT) is a condition in which IOP is elevated but no glaucomatous findings have been observed (Bell and Charleton, 2011-http://emedicine.medscape.com/article/1207470-overview). The Ocular Hypertension Study demonstrated that patients with OHT have an overall risk of 10% over 5 years of developing glaucoma and that this risk can be cut in half by the institution of medical treatment that reduces IOP. Latanoprost is described in, for example, U.S. Pat. Nos. 5,296,504; 5,422,368; 6,429,229 and 7,163,959, all of which are incorporated herein by reference in their entirety.

Latanoprost has been used as a topical ophthalmic medication for controlling the progression of glaucoma or ocular hypertension by reducing intraocular pressure. It is a prostaglandin analogue that works by increasing the outflow of aqueous fluid from the eyes (through the uveoscleral tract). Latanoprost, which is marketed as Xalatan™ is indicated for the reduction of elevated intraocular pressure in patients with open-angle glaucoma or ocular hypertension.

Applicant has been conducting clinical studies with an $A_1$ agonist. These studies have been described in co-pending application WO 2010/127210. The Applicant has shown clinically significant reduction of intraocular pressure using an $A_1$ agonist in human subjects having glaucoma. The specifications of WO 2010/127210 are herein incorporated in their entirety as if individually set forth.

Applicant has recently conducted pre-clinical studies and found that the use of a combination of an $A_1$ agonist, specifically Compound A, and a prostaglandin analog, specifically latanoprost, provided significant IOP reduction in normotensive monkeys.

SUMMARY OF THE INVENTION

There remains a need for new treatments and therapies for elevated intraocular pressure (IOP), and conditions caused by elevated IOP. There is also a need for compounds useful in the treatment or prevention or amelioration of one or more symptoms of elevated IOP and conditions caused by elevated IOP.

Thus, provided herein is a combination therapy, comprising an effective amount of an adenosine receptor $A_1$ agonist (e.g. a compound of Formula I), and an effective amount of a prostaglandin analog (e.g. latanoprost). This combination can be useful for the treatment of one or more symptoms of elevated IOP and conditions caused by elevated IOP, e.g., glaucoma.

In a first aspect there is provided an ophthalmic combination comprising i) an adenosine receptor $A_1$ agonist and ii) a prostaglandin analog for use in reducing intraocular pressure in an eye of a subject.

In one embodiment the prostaglandin analog is selected from latanoprost, travoprost, unoprostone and bimatoprost.

In another embodiment the prostaglandin analog is latanoprost.

In one embodiment the adenosine receptor $A_1$ agonist is selected from a compound of Formula (I)

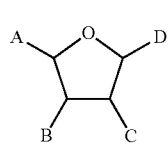

(I)

or a pharmaceutically acceptable salt thereof,
wherein
A is —$CH_2OH$, —$CH_2ONO_2$ or —$CH_2OSO_3H$;
B and C are —OH;
D is

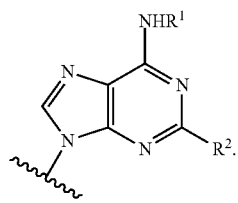

In a further embodiment the compound of Formula I is selected from:
Compound A [((2R,3S,4R,5R)-5-(6-(cyclopentylamino)-9H-purin-9-yl)-3,4-dihydroxytetrahydrofuran-2-yl)methyl nitrate];
Compound B [((2R,3S,4R,5R)-5-(2-chloro-6-(cyclopentylamino)-9H-purin-9-yl)-3,4-dihydroxytetrahydrofuran-2-yl)methyl nitrate];
Compound C [sodium ((2R,3S,4R,5R)-5-(6-(cyclopentylamino)-9H-purin-9-yl)-3,4-dihydroxytetrahydrofuran-2-yl)methyl sulfate];
Compound D [((2R,3S,4R,5R)-3,4-dihydroxy-5-(6-(tetrahydrofuran-3-ylamino)-9H-purin-9-yl)tetrahydrofuran-2-yl)methyl nitrate];
Compound E [((2R,3S,4R,5R)-5-(6-(cyclohexylamino)-9H-purin-9-yl)-3,4-dihydroxytetrahydrofuran-2-yl)methyl nitrate];
Compound F [((2R,3S,4R,5R)-5-(6-(bicycle-[2.2.1]-heptan-2-ylamino)-9H-purin-9-yl)-3,4-dihydroxytetrahydrofuran-2-yl)methyl nitrate];
Compound G [sodium ((2R,3S,4R,5R)-5-(2-chloro-6-(cyclohexylamino)-9H-purin-9-yl)-3,4-dihydroxytetrahydrofuran-2-yl)methyl sulfate];
Compound H [((2R,3S,4R,5R)-5-(2-chloro-6-(cyclohexylamino)-9H-purin-9-yl)-3,4-dihydroxytetrahydrofuran-2-yl)methyl nitrate];
Compound I [(2R,3R,4S,5R)-2-(6-(cyclopentylamino)-9H-purin-9-yl)-5-(hydroxymethyl)tetrahydrofuran-3,4-diol (N6 Cyclopentyl adenosine (CPA))]; and
Compound J [(2R,3R,4S,5R)-2-(2-chloro-6-(cyclopentylamino)-9H-purin-9-yl)-5-(hydroxymethyl)tetrahydrofuran-3,4-diol (N6 Cyclopentyl adenosine (COPA))], or a pharmaceutically acceptable salt thereof.

In a further embodiment the adenosine receptor $A_1$ agonist is Compound A, ((2R,3S,4R,5R)-5-(6-(cyclopentylamino)-9H-purin-9-yl)-3,4-dihydroxytetrahydrofuran-2-yl)methyl nitrate, or a pharmaceutically acceptable salt thereof.

In still another embodiment of the ophthalmic combination, the adenosine receptor $A_1$ agonist is Compound A, ((2R,3S,4R,5R)-5-(6-(cyclopentylamino)-9H-purin-9-yl)-3,4-dihydroxytetrahydrofuran-2-yl)methyl nitrate, or a pharmaceutically acceptable salt thereof, and the prostaglandin analog Latanoprost.

In another embodiment the $A_1$ agonist is applied to an eye of the subject simultaneously to, separately from, or sequentially with the application of the prostaglandin analog to the eye of the subject.

In a further embodiment the combination is achieved by applying one or more drops of about 0.05 mg/ml to about 7.0 mg/ml of an $A_1$ agonist with about 30 μg/ml to about 50 μg/ml of a prostaglandin analog to an eye of the subject from 1 to 4 times daily.

In a further embodiment the combination is achieved by applying about 20-700 μg of an $A_1$ agonist to an eye of the subject from 1 to 2 times daily.

In a further embodiment the combination is achieved by applying about 20-350 μg of an $A_1$ agonist to an eye of the subject from 1 to 2 times daily. In one embodiment the $A_1$ agonist and the prostaglandin analog are administered topically as one or more eye drops to the eye of the subject.

In a further aspect there is provided a method of reducing IOP and associated diseases and conditions caused by elevated IOP in a subject by administering an effective amount of a combination as defined above to an affected eye of the subject.

In one embodiment the diseases and conditions caused by elevated IOP in a human are selected from the group consisting of normal-tension glaucoma, OHT, and POAG.

In a further aspect there is provided a kit comprising i) an adenosine receptor $A_1$ agonist and ii) a prostaglandin analog for use in reducing intraocular pressure in an eye of a subject.

In one embodiment of the kit the prostaglandin analog is selected from latanoprost, travoprost, unoprostone and bimatoprost.

In another embodiment of the kit the prostaglandin analog is latanoprost.

In a further embodiment of the kit the adenosine receptor $A_1$ agonist is selected from a compound of Formula (I)

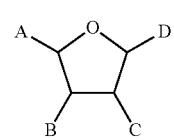

(I)

or a pharmaceutically acceptable salt thereof, wherein
A is —CH$_2$OH, —CH$_2$ONO$_2$ or —CH$_2$OSO$_3$H;
B and C are —OH;
D is

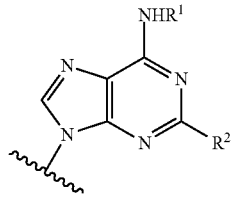

In another embodiment of the kit the compound of Formula I is selected from:

Compound A, Compound B, Compound C, Compound D, Compound E, Compound F, Compound H, or Compound I.

In another embodiment of the kit, the adenosine receptor A$_1$ agonist is Compound A, ((2R,3S,4R,5R)-5-(6-(cyclopentylamino)-9H-purin-9-yl)-3,4-dihydroxytetrahydrofuran-2-yl)methyl nitrate or a pharmaceutically acceptable salt thereof.

In still another embodiment of the kit, the adenosine receptor A$_1$ agonist is Compound A, ((2R,3S,4R,5R)-5-(6-(cyclopentylamino)-9H-purin-9-yl)-3,4-dihydroxytetrahydrofuran-2-yl)methyl nitrate, and the prostaglandin analog Latanoprost.

In one embodiment provided herein is a method of treating elevated IOP and associated diseases and conditions caused by elevated IOP in a subject by administering an effective amount of a combination comprising the adenosine receptor A$_1$ agonist Compound A, ((2R,3S,4R,5R)-5-(6-(cyclopentylamino)-9H-purin-9-yl)-3,4-dihydroxytetrahydrofuran-2-yl) methyl nitrate, and the prostaglandin analog Latanoprost.

It is to be further appreciated that the combinations or kits, as defined above, may be used in the manufacture of a medicament for reducing IOP or the treatment of conditions associated with elevated IOP, in an affected eye of a human subject. It is to be further appreciated that the combinations or kits, as defined above, may be used in the manufacture of a medicament for treating glaucoma in an affected eye of a human subject.

In one embodiment provided herein is the use of a combination of the adenosine receptor A$_1$ agonist Compound A, ((2R,3S,4R,5R)-5-(6-(cyclopentylamino)-9H-purin-9-yl)-3,4-dihydroxytetrahydrofuran-2-yl)methyl nitrate, and the prostaglandin analog Latanoprost in the manufacture of a medicament for the treatment of elevated IOP and the treatment of associated diseases and conditions caused by elevated IOP.

In another aspect of the invention is provided a combination therapy, comprising an effective amount of an adenosine receptor A$_1$ agonist, and an effective amount of a prostaglandin analog.

In one embodiment, the combination therapy is for the treatment of elevated IOP. In one embodiment, the combination therapy is for the treatment of glaucoma.

The foregoing brief summary broadly describes the features and technical advantages of certain embodiments of the present invention. Further technical advantages will be described in the detailed description of the invention that follows. Novel features which are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to be definitions of the invention's scope.

DETAILED DESCRIPTION OF THE INVENTION

Figure 1:
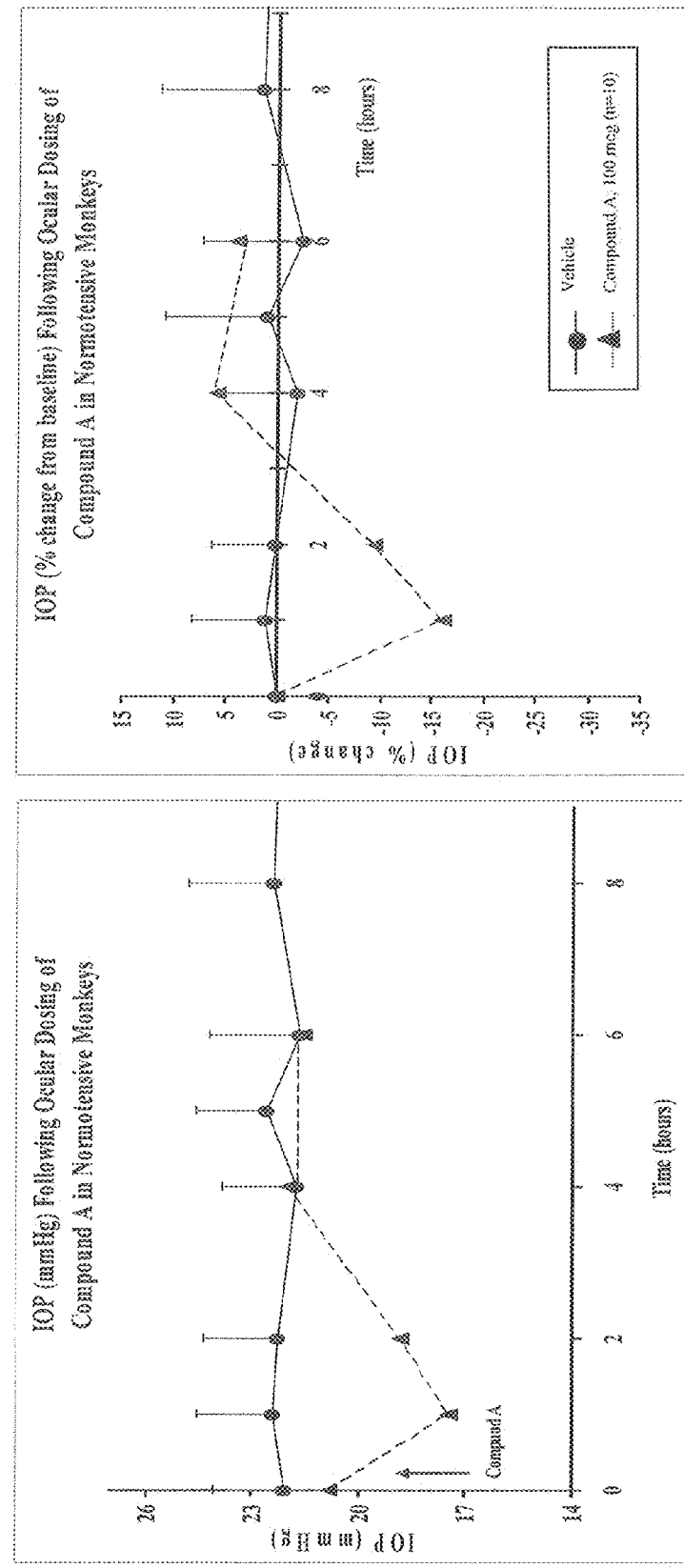
FIG. 1: shows the reduction in IOP (mmHg) in normotensive monkeys following ocular dosing of 100 mcg of Compound A at 4 hrs after ocular dosing of a prostaglandin analog compared to the reduction in IOP following dosing of a prostaglandin analog alone.

Provided herein is a combination therapy, comprising an effective amount of an adenosine receptor A$_1$ agonist (e.g., a compound of Formula I), and an effective amount of a prostaglandin analog (e.g. latanoprost, travoprost, unoprostone and bimatoprost). The combination can be used for reducing intraocular pressure in an eye of a subject in need thereof. The combination can also be useful for the treatment of diseases and conditions caused by elevated IOP in a human, such as glaucoma (e.g., normal-tension glaucoma), OHT, and POAG.

Compounds and Methods of Treatment

Compounds of Formula I have the following structure:

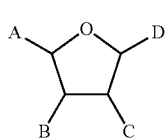

(I)

or a pharmaceutically acceptable salt thereof,
wherein
A is —CH$_2$OH, —CH$_2$ONO$_2$ or —CH$_2$OSO$_3$H;
B and C are —OH;
D is

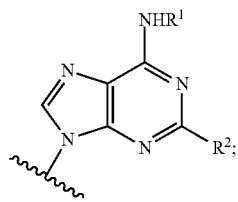

A and B are trans with respect to each other;
B and C are cis with respect to each other;
C and D are cis or trans with respect to each other;
R$^1$ is —H, —C$_1$-C$_{10}$ alkyl, -aryl, -3- to 7-membered monocyclic heterocycle, -8- to 12-membered bicyclic heterocycle, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl-(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), or —(CH$_2$)$_n$-aryl;
R$^2$ is —H, halo, —CN, —NHR$^4$, —NHC(O)R$^4$, —NHC(O)OR$^4$, —NHC(O)NHR$^4$, —NHNHC(O)R$^4$, —NHNHC(O)OR$^4$, —NHNHC(O)NHR$^4$, or —NH—N═C(R$^6$)R$^7$;
R$^4$ is —C$_1$-C$_{15}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;
R$^6$ is —C$_1$-C$_{10}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$—(C$_3$-C$_8$ monocyclic cycloalkenyl), -phenylene-(CH$_2$)$_n$COOH, or -phenylene-(CH$_2$)$_n$COO—(C$_1$-C$_{10}$ alkyl);
R$^7$ is —H, —C$_1$-C$_{10}$ alkyl, -aryl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkenyl) or —(CH$_2$)$_n$—(C$_8$-C$_{12}$ bicyclic cycloalkyl) and each n is independently an integer ranging from 1 to 5.

In a further embodiment, compounds of Formula I are of the Formula Ia:

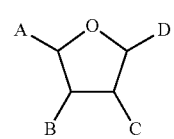

(Ia)

or a pharmaceutically acceptable salt thereof,
wherein
A is —CH$_2$ONO$_2$ or —CH$_2$OSO$_3$H;
B and C are —OH;
D is

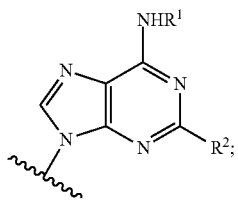

A and B are trans with respect to each other;
B and C are cis with respect to each other;
C and D are cis or trans with respect to each other;
R$^1$ is —C$_3$-C$_8$ monocyclic cycloalkyl, -3- to 7-membered monocyclic heterocycle, or —C$_8$-C$_{12}$ bicyclic cycloalkyl; and
R$^2$ is —H or -halo.

In yet another embodiment, compounds of Formula I are of the Formula Ib:

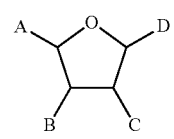

(Ib)

or a pharmaceutically acceptable salt thereof,
wherein
A is —CH$_2$ONO$_2$;
B and C are —OH;
D is

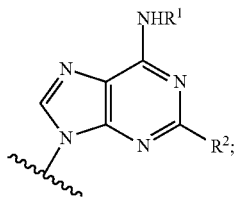

A and B are trans with respect to each other;
B and C are cis with respect to each other;
C and D are cis or trans with respect to each other;

R[1] is —$C_3$-$C_8$ monocyclic cycloalkyl, -3- to 7-membered monocyclic heterocycle, or —$C_8$-$C_{12}$ bicyclic cycloalkyl; and R[2] is —H or -halo.

In a further embodiment the compound of Formula I is selected from:

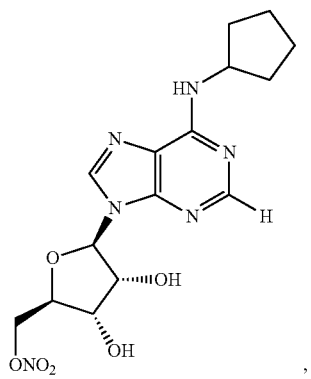

Compound A ((2R,3S,4R,5R)-5-(6-(cyclopentylamino)-9H-purin-9-yl)-3,4-dihydroxytetrahydrofuran-2-yl)methyl nitrate

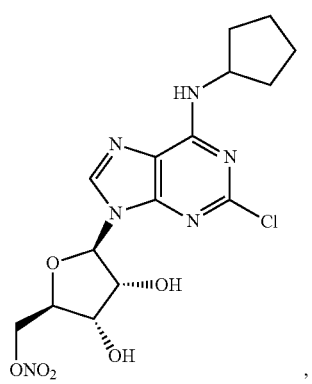

Compound B ((2R,3S,4R,5R)-5-(2-chloro-6-(cyclopentylamino)-9H-purin-9-yl)-3,4-dihydroxytetrahydrofuran-2-yl)methyl nitrate

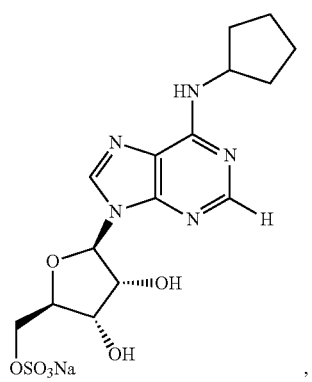

Compound C sodium ((2R,3S,4R,5R)-5-(6-(cyclopentylamino)-9H-purin-9-yl)-3,4-dihydroxytetrahydrofuran-2-yl)methyl sulfate

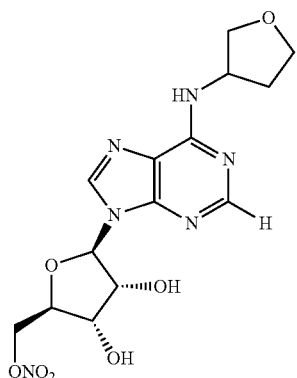

Compound D ((2R,3S,4R,5R)-3,4-dihydroxy-5-(6-(tetrahydrofuran-3-ylamino)-9H-purin-9-yl)tetrahydrofuran-2-yl) methyl nitrate

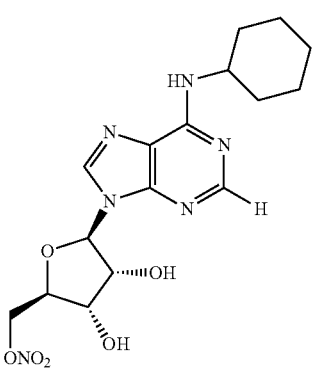

Compound E ((2R,3S,4R,5R)-5-(6-(cyclohexylamino)-9H-purin-9-yl)-3,4-dihydroxytetrahydrofuran-2-yl) methyl nitrate

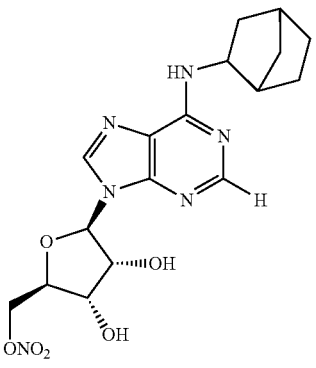

Compound F ((2R,3S,4R,5R)-5-(6-(bicycle)-[2.2.1]-heptan-2-ylamino-9H-purin-9-yl)-3,4-dihydroxytetrahydrofuran-2-yl) methyl nitrate Compound G

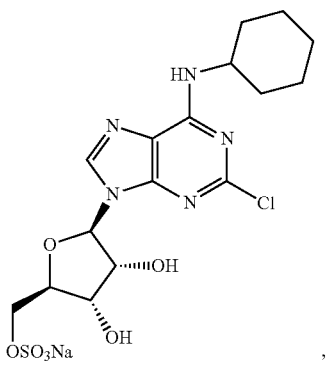

sodium ((2R,3S,4R,5R)-5-(2-chloro-6-
(cyclohexylamino)-9H-purin-9-yl)-
3,4-dihydroxytetrahydrofuran-2-yl)
methyl sulfate Compound H

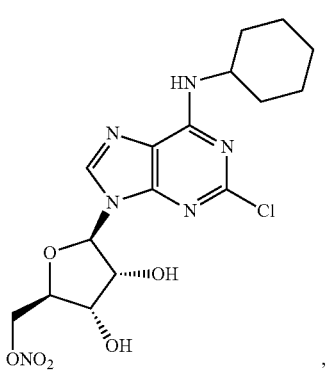

((2R,3S,4R,5R)-5-(2-chloro-6-
(cyclohexylamino)-9H-purin-9-yl)-
3,4-dihydroxytetrahydrofuran-2-yl)
methyl nitrate Compound I

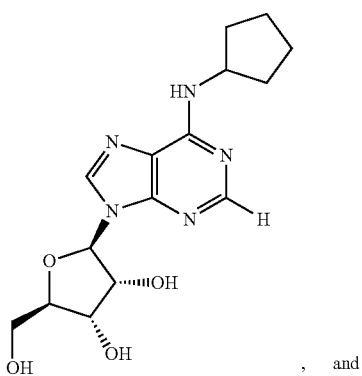

(2R,3R,4S,5R)-2-(6-
(cyclopentylamino)-9H-purin-9-yl)-
5-(hydroxymethyl)tetrahydrofuran-
3,4-diol (N6 Cyclopentyl adenosine
(CPA))

Compound J

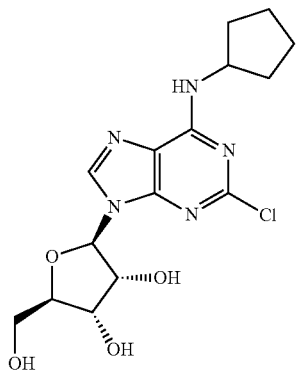

(2R,3R,4S,5R)-2-(2-chloro-6-(cyclopentylamino)-9H-purin-9-yl)-5-(hydroxymethyl)tetrahydrofuran-3,4-diol (N6 Cyclopentyl adenosine (CCPA)), or a pharmaceutically acceptable salt thereof.

In a further embodiment the adenosine receptor $A_1$ agonist is Compound A, ((2R,3S,4R,5R)-5-(6-(cyclopentylamino)-9H-purin-9-yl)-3,4-dihydroxytetrahydrofuran-2-yl)methyl nitrate, or a pharmaceutically acceptable salt thereof.

In still another embodiment of the ophthalmic combination, the adenosine receptor $A_1$ agonist is Compound A, ((2R,3S,4R,5R)-5-(6-(cyclopentylamino)-9H-purin-9-yl)-3,4-dihydroxytetrahydrofuran-2-yl)methyl nitrate, and the prostaglandin analog Latanoprost.

It may be helpful to provide definitions of certain terms to be used herein. Unless defined otherwise, all technical and scientific terms used herein have the same meaning as is commonly understood by one of skill in the art to which this invention belongs.

The invention provides for a combination of therapeutic agents and administration of the combination of agents to treat elevated intraocular pressure (IOP), as well as conditions caused by elevated IOP. A used herein, a "combination of agents" and similar terms refer to a combination of two types of agents: (1) adenosine receptor $A_1$ agonists (e.g. compounds of Formula I) and/or pharmacologically active metabolites, salts, solvates and racemates of adenosine receptor $A_1$ agonists and (2) prostaglandin analogs (e.g. latanoprost) and/or pharmacologically active metabolites, salts, solvates and racemates of prostaglandin analogs. Pharmacologically active metabolites include those that are inactive but are converted into pharmacologically active forms in the body after administration.

Administration of the combination includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agents as compared to the other agent in the combination. Therefore, to permit appropriate dosing, packaged pharmaceutical products may contain one or more dosage forms that contain the combination of agents, and one or more dosage forms that contain one of the combinations of agents, but not the other agent(s) of the combination.

An "effective amount" of a combination of agents (e.g. an adenosine receptor $A_1$ agonist and a prostaglandin analog) is an amount sufficient to provide an observable improvement over the baseline clinically observable signs and symptoms of the depressive disorder treated with the combination.

The term "treat" is used herein to mean to relieve, reduce or alleviate at least one symptom of a disease in a subject. For example, in relation to glaucoma, the term "treat" may mean to reduce or alleviate elevated intraocular pressure. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent, delay or treat, or all, as appropriate, development or continuance or aggravation of a disease in a subject.

The term "subject" is intended to include animals, which are capable of suffering from or afflicted with elevated IOP, as well as conditions caused by elevated IOP. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from IOP, or conditions caused by elevated IOP.

The term "about" or "approximately" usually means within 20%, more preferably within 10%, and most preferably still within 5% of a given value or range. Alternatively, especially in biological systems, the term "about" means within about a log(i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

Embodiments of the present invention provide combinations useful for treating reducing and controlling normal or elevated intraocular pressure (IOP) and/or treating glaucoma.

Adenosine is a purine nucleoside that modulates many physiologic processes. Cellular signaling by adenosine occurs through four adenosine receptor subtypes: $A_1$, $A_{2A}$, $A_{2B}$, and $A_3$ as reported by Ralevic and Burnstock (Pharmacol Rev. 50:413-492, 1988) and Fredholm B B et al (Pharmacol Rev. 53:527-552, 2001). In the eye, adenosine $A_1$ receptor agonists lower IOP in mice, rabbits and monkeys (Tian B et al. Exp Eye Res. 64:979-989, 1997; Crosson C E. J Pharmacol Exp Ther. 273: 320-326, 1995; and Avila M Y et al. Br J. Pharmacol. 134:241-245, 2001). While other publications have noted that adenosine A1 receptor agonists in the eye target the conventional outflow pathway via the trabecular meshwork (Husain S et al. J Pharmacol Exp Ther. 320: 258-265, 2007), reduction of IOP via other pathways has not been excluded.

In one embodiment, provided herein is an ophthalmic combination or kit for use in reducing intraocular pressure, comprising i) an adenosine receptor $A_1$ agonist and ii) a prostaglandin analog for use in reducing intraocular pressure in an eye of a subject. In one embodiment the prostaglandin analog is selected from latanoprost, travoprost, unoprostone and bimatoprost. In another embodiment the prostaglandin analog is latanoprost. In another embodiment provided herein the $A_1$ agonist is Compound A. In another embodiment, provided herein is a method of treating normal-tension glaucoma, comprising administering to an affected eye of a subject an effective amount of a combination of Compound A and latanoprost. In another embodiment, provided herein is a method of treating OHT, comprising administering to an affected eye of a subject an effective amount of a combination of Compound A and latanoprost. In another embodiment, provided herein is a method of treating POAG, comprising administering to an affected eye of a subject an effective amount of a combination of Compound A and latanoprost. In one embodiment of the combination, about 0.05 mg/ml to about 7.0 mg/ml of Compound A is applied to an affected eye of a subject from 1 to 4 times daily. In one embodiment, about 20-700 μg of Compound A is applied to an affected eye of a subject from 1 to 4 times daily. In one embodiment, about 20-350 μg of Compound A is applied to an affected eye of a subject from 1 to 4 times daily. The Compound A can be administered in drops, e.g., 1 to 2 drops. In one embodiment about 30 μg/ml to about 50 μg/ml of the prostaglandin is applied to an affected eye. In one embodiment the subject is a human.

It is recognized that compounds of Formula I can contain one or more chiral centers. This invention contemplates all enantiomers, diastereomers, and mixtures of Formulas I thereof.

Furthermore, certain embodiments of the present invention comprise pharmaceutically acceptable salts of compounds according to Formula I. Pharmaceutically acceptable salts comprise, but are not limited to, soluble or dispersible forms of compounds according to Formula I that are suitable for treatment of disease without undue undesirable effects such as allergic reactions or toxicity. Representative pharmaceutically acceptable salts include, but are not limited to, acid addition salts such as acetate, citrate, benzoate, lactate, or phosphate and basic addition salts such as lithium, sodium, potassium, or aluminum.

As used herein, the term "$A_1$ agonist" means an $A_1$ agonist that has an affinity to the $A_1$ receptor while simultaneously having a lower affinity for the $A_2$ and $A_3$ adenosine receptors. Compounds A to J as described herein have affinities to the A1 receptor considerably greater than their respective affinities to the $A_2A$ and $A_3$ receptors. The $A_1$ selectivity data for compounds A to J is summarized in the Table below.

| Compound | $A_1$ (Ki (nm)) POTENCY | $A_1 > A_{2A}$ SELECTIVITY [$KiA_2$ (nm)/$KiA_1$ (nm)] | $A_1 > A_3$ SELECTIVITY [$KiA_3$ (nm)/ $KiA_1$ (nm)] |
|---|---|---|---|
| Compound A | 0.97 | 4837 | 725 |
| Compound B | 2.63 | 1593 | 195 |
| Compound C | 4.05 | 2250 | 251 |
| Compound D | 10.6 | >9434 | 202 |
| Compound E | 1.32 | 878 | 1098 |
| Compound F | 1.47 | 3945 | 260 |
| Compound G | 1.36 | 200 | 130 |
| Compound H | 8 | 192 | 167 |
| Compound I | 2.3 | 345 | 31.3 |
| Compound J | 0.83 | 2735 | 50 |

Methods that can be used to synthesize these compounds are described below.

The term "$C_1$-$C_{15}$ alkyl" as used herein refers to a straight or branched chain, saturated hydrocarbon having from 1 to 15 carbon atoms. Representative $C_1$-$C_{15}$ alkyl groups include, but are not limited to methyl, ethyl, propyl, isopropyl, butyl, sec-butyl, tert-buty, pentyl, isopentyl, neopentyl, hexyl, isohexyl, neohexyl, heptyl, isoheptyl, neoheptyl, octyl, isooctyl, neooctyl, nonyl, isononyl, neononyl, decyl, isodecyl, neodecyl, undecyl, dodecyl, tridecyl, tetradecyl and pentadecyl. In one embodiment, the $C_1$-$C_{15}$ alkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_1$-$C_{15}$ alkyl is unsubstituted.

The term "$C_1$-$C_{10}$ alkyl" as used herein refers to a straight or branched chain, saturated hydrocarbon having from 1 to 10 carbon atoms. Representative $C_1$-$C_{10}$ alkyl groups include, but are not limited to methyl, ethyl, propyl, isopropyl, butyl, sec-butyl, tert-butyl, pentyl, isopentyl, neopentyl, hexyl, isohexyl, neohexyl, heptyl, isoheptyl, neoheptyl, octyl, isooctyl, neooctyl, nonyl, isononyl, neononyl, decyl, isodecyl and neodecyl. In one embodiment, the $C_1$-$C_{10}$ alkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_1$-$C_{10}$ alkyl is unsubstituted.

The term "$C_1$-$C_6$ alkyl" as used herein refers to a straight or branched chain, saturated hydrocarbon having from 1 to 6 carbon atoms. Representative $C_1$-$C_6$ alkyl groups include, but are not limited to methyl, ethyl, propyl, isopropyl, butyl, sec-butyl, tert-buty, pentyl, isopentyl, neopentyl, hexyl, isohexyl, and neohexyl. Unless indicated, the C1-C6 alkyl is unsubstituted.

The term "aryl" as used herein refers to a phenyl group or a naphthyl group. In one embodiment, the aryl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the aryl is unsubstituted.

The term "$C_3$-$C_8$ monocyclic cycloalkyl" as used herein is a 3-, 4-, 5-, 6-, 7- or 8-membered saturated non-aromatic monocyclic cycloalkyl ring. Representative $C_3$-$C_8$ monocyclic cycloalkyl groups include, but are not limited to, cyclopropyl, cyclobutyl, cyclopentyl, cyclohexyl, cycloheptyl and cyclooctyl. In one embodiment, the $C_3$-$C_8$ monocyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkyl is unsubstituted.

The term "$C_3$-$C_8$ monocyclic cycloalkenyl" as used herein is a 3-, 4-, 5-, 6-, 7- or 8-membered non-aromatic monocyclic carbocyclic ring having at least one endocyclic double bond, but which is not aromatic. It is to be understood that when any two groups, together with the carbon atom to which they are attached form a $C_3$-$C_8$ monocyclic cycloalkenyl group, the carbon atom to which the two groups are attached remains tetravalent. Representative $C_3$-$C_8$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl, 1,3,5-cycloheptatrienyl, cyclooctenyl, 1,3-cyclooctadienyl, 1,4-cyclooctadienyl, 1,3,5-cyclooctatrienyl. In one embodiment, the $C_3$-$C_8$ monocyclic cycloalkenyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkenyl is unsubstituted.

The term "$C_8$-$C_{12}$ bicyclic cycloalkyl" as used herein is a 8-, 9-, 10-, 11- or 12-membered saturated, non-aromatic bicyclic cycloalkyl ring system. Representative $C_8$-$C_{12}$ bicyclic cycloalkyl groups include, but are not limited to, decahydronaphthalene, octahydroindene, decahydrobenzocycloheptene, and dodecahydroheptalene. In one embodiment, the $C_8$-$C_{12}$ bicyclic cycloalkyl group is substituted with one or more of the following groups: -halo, —O—($C_1$-$C_6$ alkyl), —OH, —CN, —COOR', —OC(O)R', —N(R')$_2$, —NHC(O)W or —C(O)NHR' groups wherein each R' is independently —H or unsubstituted —$C_1$-$C_6$ alkyl. Unless indicated, the $C_8$-$C_{12}$ bicyclic cycloalkyl is unsubstituted.

The term "$C_8$-$C_{12}$ bicyclic cycloalkenyl" as used herein is a 8-, 9-, 10-, 11- or 12-membered non-aromatic bicyclic cycloalkyl ring system, having at least one endocyclic double bond. It is to be understood that when any two groups, together with the carbon atom to which they are attached form a $C_8$-$C_{12}$ bicyclic cycloalkenyl group, the carbon atom to which the two groups are attached remains tetravalent. Representative $C_8$-$C_{12}$ bicyclic cycloalkenyl groups include, but are not limited to, octahydronaphthalene, hexahydronaphthalene, hexahydroindene, tetrahydroindene, octahydrobenzocycloheptene, hexahydrobenzocycloheptene, tetrahydrobenzocycloheptene, decahydroheptalene, octahydroheptalene, hexahydroheptalene, and tetrahydroheptalene. In one embodiment, the $C_8$-$C_{12}$ bicyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_8$-$C_{12}$ bicyclic cycloalkenyl is unsubstituted.

The term "effective amount" as used herein refers to an amount of a selective adenosine receptor $A_1$ agonist that is effective for: (i) treating or preventing elevated IOP; or (ii) reducing IOP in a human.

The term "halo" as used herein refers to —F, —Cl, —Br or —I.

The term "3- to 7-membered monocyclic heterocycle" refers to: (i) a 3- or 4-membered non-aromatic monocyclic cycloalkyl in which 1 of the ring carbon atoms has been replaced with an N, O or S atom; or (ii) a 5-, 6-, or 7-membered aromatic or non-aromatic monocyclic cycloalkyl in which 1-4 of the ring carbon atoms have been independently replaced with a N, O or S atom. The non-aromatic 3- to 7-membered monocyclic heterocycles can be attached via a ring nitrogen, sulfur, or carbon atom. The aromatic 3- to 7-membered monocyclic heterocycles are attached via a ring carbon atom. Representative examples of a 3- to 7-membered monocyclic heterocycle group include, but are not limited to furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl, In one embodiment, the 3- to 7-membered monocyclic heterocycle group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the 3- to 7-membered monocyclic heterocycle is unsubstituted.

The term "8- to 12-membered bicyclic heterocycle" refers to a bicyclic 8- to 12-membered aromatic or non-aromatic bicyclic cycloalkyl in which one or both of the of the rings of the bicyclic ring system have 1-4 of its ring carbon atoms independently replaced with a N, O or S atom. Included in this class are 3- to 7-membered monocyclic heterocycles that are fused to a benzene ring. A non-aromatic ring of an 8- to 12-membered monocyclic heterocycle is attached via a ring nitrogen, sulfur, or carbon atom. An aromatic 8- to 12-membered monocyclic heterocycles are attached via a ring carbon atom. Examples of 8- to 12-membered bicyclic heterocycles include, but are not limited to, benzimidazolyl, benzofuranyl, benzothiofuranyl, benzothiophenyl, benzoxazolyl, benzthiazolyl, benztriazolyl, benztetrzolyl, benzisoxazolyl, benzisothiazolyl, benzimidazolinyl, cinnolinyl, decahydroquinolinyl, 1H-indazolyl, indolenyl, indolinyl, indolizinyl, indolyl, isobenzofuranyl, isoindazolyl, isoindolyl, isoindolinyl, isoquinolinyl, naphthyridinyl, octahydroisoquinolinyl, phthalazinyl, pteridinyl, purinyl, quinoxalinyl, tetrahydroisoquinolinyl, tetrahydroquinolinyl, and xanthenyl. In one embodiment, each ring of a the –8- to 12-membered bicyclic heterocycle group can substituted with one or more of the following groups: -halo, —O—($C_1$-$C_6$ alkyl), —OH, —CN, —COOR', —OC(O)R', —N(R')$_2$, —NHC(O)R'. or —C(O)NHR' groups wherein each R' is independently —H or unsubstituted —$C_1$-$C_6$ alkyl. Unless indicated, the 8- to 12-membered bicyclic heterocycle is unsubstituted. Representative examples of a "phenylene group" are depicted below:

The phrase "pharmaceutically acceptable salt," as used herein, is a salt of an acid and a basic nitrogen atom of a purine compound. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The pharmaceutically acceptable salt can also be a camphorsulfonate salt. The term "pharmaceutically acceptable salt" also refers to a salt of a purine compound having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. The term "pharmaceutically acceptable salt" also includes a hydrate of a purine compound. Some chemical structures herein are depicted using bold and dashed lines to represent chemical bonds. These bold and dashed lines depict absolute stereochemistry. A bold line indicates that a substituent is above the plane of the carbon atom to which it is attached and a dashed line indicates that a substituent is below the plane of the carbon atom to which it is attached.

The term "subject" as used herein is a mammal, e.g., a human, mouse, rat, guinea pig, dog, cat, horse, cow, pig, or non-human primate, such as a monkey, chimpanzee or baboon. In one embodiment, the monkey is a Cynomolgus monkey. In one embodiment, the subject is a human.

The term "treat," "treated," "treating" or "treatment" includes the diminishment or alleviation of at least one symptom associated or caused by the state, disorder or disease being treated. In certain embodiments, the treatment comprises the induction of elevated IOP, followed by the activation of the compound of the invention, which would in turn diminish or alleviate at least one symptom associated or caused by the elevated IOP. For example, treatment can be diminishment of one or several symptoms of a disorder or complete eradication of a disorder.

The term "use" includes any one or more of the following embodiments of the invention, respectively: the use in the treatment of elevated IOP; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from glaucoma, POAG or OHT.

The term "about" or "approximately" usually means within 20%, more preferably within 10%, and most preferably still within 5% of a given value or range. Alternatively, especially in biological systems, the term "about" means within about a log(i.e., an order of magnitude) preferably within a factor of two of a given value.

As used herein, the term "drop" or "drops" refers to a quantity of ophthalmically acceptable fluid that resembles a liquid drop. In one embodiment, a drop refers to a liquid volume equivalent to about 5 µl to about 200 µl, e.g., about 30 µl to about 80 µl. refers to a liquid volume equivalent to about 5 µl to about 200 µl, e.g., about 30 µl to about 80 µl.

The following abbreviations are used herein and have the indicated definitions: CCPA is 2-chloro-N6-cyclopentyladenosine; CPA is N6-cyclopentyladenosine; NECA is adenosine-5'-(N-ethyl)carboxamido; NMR is nuclear magnetic resonance; R-PIA is N6-(2-phenyl-isopropyl) adenosine, R-isomer; OHT is ocular hypertension or POAG is primary open-angle glaucoma; HPβCD is hydroxypropyl β-cyclodextrin.

Dosages

The optimal dose of the combination of agents for treatment of elevated IOP can be determined empirically for each individual using known methods and will depend upon a variety of factors, including, though not limited to, the degree of advancement of the disease; the age, body weight, general health, gender and diet of the individual; the time of administration; and other medications the individual is taking. Optimal dosages may be established using routine testing and procedures that are well known in the art. Daily dosages for the compounds of formula I can be 10 µg to about 2000 µg.

The amount of combination of agents that may be combined with the carrier materials to produce a dosage form will vary depending upon the individual treated.

Frequency of dosage may vary depending on the compound used and the particular elevated IOP condition to be treated or prevented and the patient's/subject's medical history. In general, the use of the minimum dosage that is sufficient to provide effective therapy is preferred. Patients may generally be monitored for therapeutic effectiveness using assays or tests suitable for the IOP condition being treated or prevented, which will be familiar to those of ordinary skill in the art.

The dosage form can be prepared by various conventional mixing, comminution and fabrication techniques readily apparent to those skilled in the chemistry of drug formulations.

The drug compounds of the present invention (for example, a compound of formula (I), particularly compound A, and a prostaglandin analog, e.g., latanoprost) are present in the combinations, dosage forms, pharmaceutical compositions and pharmaceutical formulations disclosed herein in a ratio in the range of 100:1 to 1:100, more preferably 1:10-1:100, e.g., 1:15-1:60, e.g., 1:20-1:50 (prostaglandin analog:$A_1$ agonist).

The optimum ratios, individual and combined dosages, and concentrations of the drug compounds that yield efficacy without toxicity are based on the kinetics of the active ingredients' availability to target sites, and are determined using methods known to those of skill in the art.

Pharmaceutical Compositions

The pharmaceutical compositions or combinations provided herein (e.g., a compound of formula (I), particularly compound A, and a prostaglandin analog, e.g., latanoprost) can be tested in clinical studies. Suitable clinical studies may be, for example, open label, dose escalation studies in patients with elevated IOP. The beneficial effects on elevated IOP may be determined directly through the results of these studies which are known as such to a person skilled in the art. Such studies may be, in particular, suitable to compare the effects of a monotherapy using the active ingredients and a combination of the invention. In one embodiment, the dose of a compound of formula (I), e.g., compound A, is escalated until the Maximum Tolerated Dosage is reached, and a prostaglandin analog is administered with a fixed dose. Alternatively, a compound of formula (I), e.g., compound A, may be administered in a fixed dose and the dose of the prostaglandin analog may be escalated. Each patient may receive doses of a compound of formula (I), e.g., compound A, either daily, or twice-four times daily. The efficacy of the treatment may be determined in such studies, e.g., after 12, 18 or 24 weeks by evaluation of symptom scores every 6 weeks.

The administration of a pharmaceutical combination of the invention may result not only in a beneficial effect, e.g. with regard to alleviating, delaying progression of or inhibiting the symptoms elevated IOP, but also in further surprising beneficial effects, e.g. fewer side-effects or an improved quality of life, compared with a monotherapy applying only one of the pharmaceutically active ingredients used in the combination of the invention.

A further benefit may be that lower doses of the active ingredients of the combination of the invention may be used, for example, that the dosages need not only often be smaller but may also be applied less frequently, which may diminish the incidence or severity of side-effects. This is in accordance with the desires and requirements of the patients to be treated.

It is one objective of this invention to provide a pharmaceutical composition comprising a quantity, which may be jointly therapeutically effective at reducing IOP and/or reducing glaucoma. In this composition, a compound of formula (I) and a prostaglandin analog may be administered together, one after the other or separately in one combined unit dosage form or in two separate unit dosage forms.

The pharmaceutical compositions for separate administration of both compounds, may be prepared in a manner known per se and are those suitable for topical ocular administration to mammals (warm-blooded animals), including humans, comprising a therapeutically effective amount of at least one pharmacologically active combination partner alone, e.g. as indicated above, or in combination with one or more pharmaceutically acceptable carriers or diluents.

Formulations

The drug combinations provided herein may be formulated by a variety of methods apparent to those of skill in the art of pharmaceutical formulation. Suitable pharmaceutical formulations may contain, for example, from about 0.1% to about 99.9%, preferably from about 1% to about 60%, of the active ingredient(s). It will be appreciated that the unit content of a combination partner contained in an individual dose of each dosage form need not in itself constitute an effective amount since the necessary effective amount may be reached by administration of a plurality of dosage units.

In particular, a therapeutically effective amount of each of the combination partner of the combination of the invention may be administered simultaneously or sequentially and in any order. For example, the method of reducing IOP according to the invention may comprise (i) administration of the first agent (a) in free or pharmaceutically acceptable salt form and (ii) administration of an agent (b) in free or pharmaceutically acceptable salt form, simultaneously or sequentially in any order, in jointly therapeutically effective amounts, e.g. in daily or intermittently dosages corresponding to the amounts described herein. The individual combination partners of the combination of the invention may be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of the combination partners employed in the combination of the invention may vary depending on the particular compound or pharmaceutical composition employed, the condition being treated, the severity of the condition being treated. Thus, the dosage regimen of the combination of the invention is selected in accordance with a variety of factors including the medical history of the patient. A clinician or physician of ordinary skill can readily determine and prescribe the effective amount of the single active ingredients required to alleviate, counter or arrest the progress of the condition.

The compounds according to formula I can be incorporated into various types of ophthalmic compositions or formulations for delivery. Formula I compounds may be delivered directly to the eye (for example: topical ocular drops or ointments; slow release devices such as pharmaceutical drug delivery sponges implanted in the cul-de-sac or implanted adjacent to the sclera or within the eye; periocular, conjunctival, sub-tenons, intracameral, intravitreal, or intracanalicular injections) using techniques well known by those of ordinary skill in the art. It is further contemplated that the agents of the invention may be formulated in intraocular insert or implant devices.

The compounds of Formula I are preferably incorporated into topical ophthalmic formulations with a pH of about 4-8 for delivery to the eye. One such formulation is an aqueous suspension formulation described in detail in PCT/US2010/054040, and outlined below in the examples. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity or solubility such as hydroxypropyl β-Cyclodextrin (HPβCD), hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient may be combined with a preservative in an appropriate vehicle such as mineral oil, liquid lanolin, or white petrolatum. Sterile ophthalmic gel formulations may be prepared by suspending the compound in a hydrophilic base prepared from the combination of, for example, carbopol-974, or the like, according to the published formulations for analogous ophthalmic preparations; preservatives and tonicity agents can be incorporated.

Compounds in preferred embodiments are contained in a composition in amounts sufficient to lower IOP in patients experiencing elevated IOP and/or maintaining normal IOP levels in POAG or OHT patients. Such amounts are referred to herein as "an amount effective to control or reduce IOP," or more simply "an effective amount." The compounds will normally be contained in these formulations in an amount 0.05 mg/ml to 7.0 mg/ml but preferably in an amount of 0.4 to 7.0 mg/ml. Thus, for topical presentation 1 to 2 drops of these formulations would be delivered to the surface of the eye from 1 to 4 times per day, according to the discretion of a skilled clinician.

Methods of Synthesis

Compounds according to Formula I can be prepared by using synthetic procedures described in U.S. Pat. No. 7,423,144, the disclosure of which is incorporated herein in its entirety, as well as other published methods (see Cristalli et al., *J. Med. Chem.* 35:2363-2369, 1992; Cristalli et al., *J. Med. Chem.* 37:1720-1726, 1994; Cristalli et al, *J. Med. Chem.* 38:1462-1472, 1995; and Camaioni et al., *Bioorg. Med. Chem.* 5:2267-2275, 1997), or by using the synthetic procedures outlined below.

Scheme 1 shows methods for making nucleoside intermediates that are useful for making the compounds of the invention.

Scheme 1

1

-continued

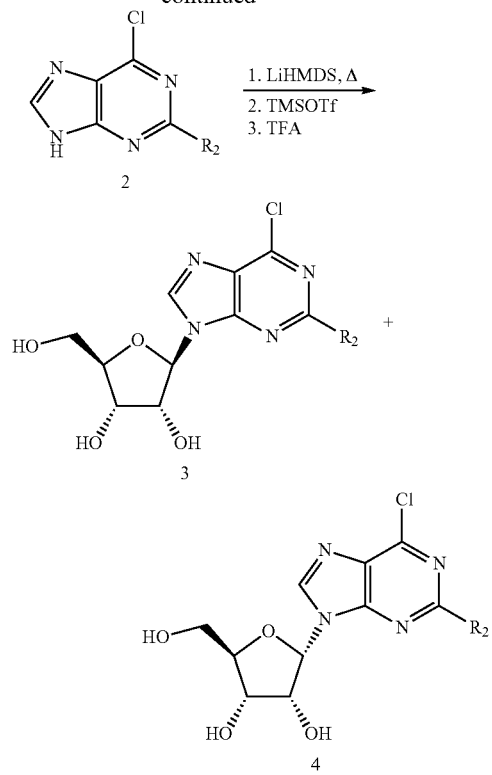

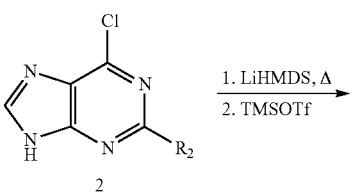

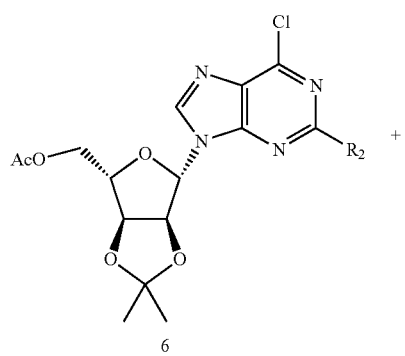

-continued

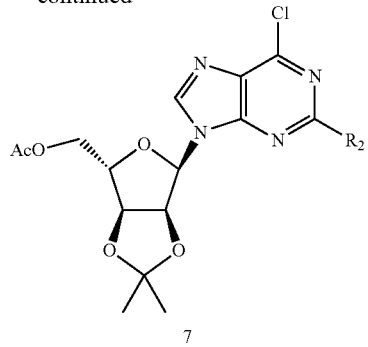

7 wherein R₂ is as defined above.

The protected ribose compound of Formula 1 can be coupled with a purine compound of Formula 2 using lithium hexamethyldisilazide and trimethylsilyl triflate, followed by acetonide removal using trifluoroacetic acid to provide nucleoside intermediates of Formula 3 and their corresponding other anomers of Formula 4. Similarly, the ribose diacetate of Formula 5 can be coupled with a compound of Formula 2 using lithium hexamethyldisilazide and trimethylsilyl triflate to provide acetonide-protected nucleoside intermediates of Formula 6 and their corresponding other anomers of Formula 7.

Scheme 2 shows a method useful for making the adenosine intermediates of Formula 8 which are useful for making the compounds of the invention.

Scheme 2

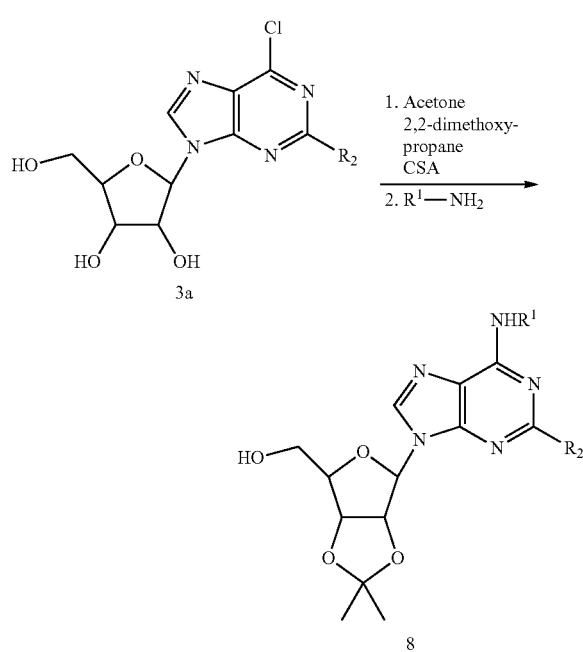

where $R^1$ and $R^2$ are defined above.

The 6-chloroadenosine derivative of formula 3a is converted to its 2',3'-acetonide using acetone and 2,2-dimethoxypropane in the presence of camphorsulfonic acid. The acetonide can be further derviatized using an amine of formula $R^1$—$NH_2$ in the presence of base to provide compounds of formula 8.

Methodology useful for making other compounds of the invention is described in Scheme 4.

Scheme 4

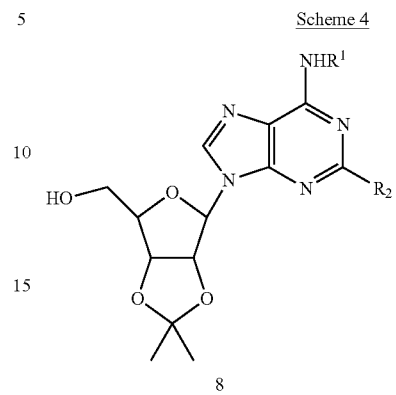

8

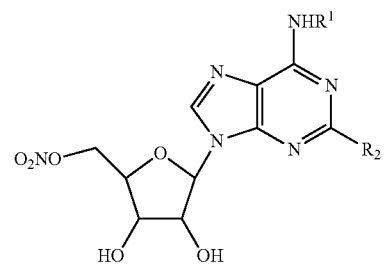

where $R^1$ and $R^2$ are defined above.

The adenosine intermediates of formula 8 can be converted to their 5'-nitrate analogs using nitric acid in the presence of acetic anhydride, or other nitrating agents, such as MsCl/ONO₃ or nitrosonium tetrafluoroborate. Acetonide removal using TFA/water provides compounds of the invention.

Methodology useful for making the Purine Derivatives of Formula (Id) wherein $R^3$ is —$CH_2OSO_3H$ is outlined in Scheme 6.

Scheme 6

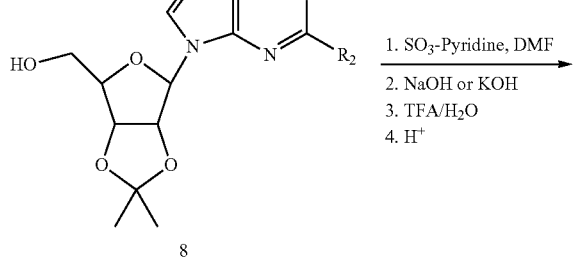

8

-continued

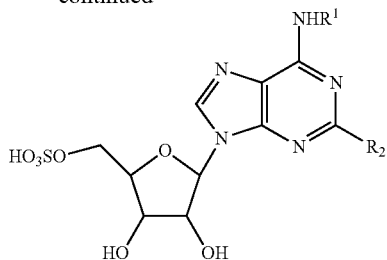

where R¹ and R² are defined above.

The adenosine intermediates of formula 8 can be treated with sulfur trioxide-pyridine complex to provide the corresponding 5'-sulfonic acid pyridine salt intermediate. The pyridine salt intermediate can then be neutralized using NaOH or KOH, followed by acetonide removal using TFA/water to provide the corresponding sodium or potassium salt, respectively, of the Purine Derivatives of Formula (Id) wherein A is —CH$_2$OSO$_3$H. Treatment of the sodium or potassium salt with strong aqueous acid, such as sulfuric or hydrochloric acid, provides compounds of the invention wherein A is —CH$_2$OSO$_3$H.

EXAMPLES/EXPERIMENTAL

The experiments were conducted in ten conscious cynomolgus monkeys (*Macaca fascicularis*). The monkeys were without ocular disease and had intraocular pressure readings in the normal range, and were classed as normotensive monkeys. Prior to the study, the monkeys were previously acclimated to the study procedures (e.g., dosing, tonometry, ocular examinations, and handling), and allowed a washout period before each treatment.

Compound A was administered in two different formulations:
1. HPβCD (hydroxypropyl-β-cyclodextrin) Formulation
   In one formulation, lyophilized Compound A to HPβCD in 1:20 (wt/wt) was reconstituted with 0.9% Saline for Injection, USP.
2. Aqueous Suspension Formulation
   The aqueous formulation comprised of the following:

| Ingredient | %, w/v |
| --- | --- |
| Compound A, micronized | 2.0 |
| Sodium CMC, low viscosity | 0.7 |
| Benzalkonium Chloride | 0.01 |
| Polysorbate 80 | 0.3 |
| Citric Acid Monohydrate | 0.15 (7 mM) |
| NaCl | 0.8% (qs to 290-300 mOsm) |
| NaOH/HCl (pH adjustment) | pH 5.1 ± 0.1 |
| Purified Water | q.s. 100 |

Treatment 1
In the first treatment, 10 monkeys received topically 100 mcg of Compound A at 40 mcL, formulated in an aqueous suspension in one study eye and vehicle/placebo control applied topically in the contralateral eye. During the study, the intraocular pressures (IOP) of both the study eye and contralateral eye were measured repeatedly using a calibrated pneumotonometer following an application of a topical anesthetic (proparacaine). The control in the first treatment was a 40 mcL composition of 0.8% sodium chloride (NaCl), 0.15% citrate, 0.01% benzalkonium chloride, 0.3% polysorbate 80, and 0.7% sodium (Na) carboxymethylcellulose.

Treatment 2
In the second treatment, 10 monkeys received latanoprost (Xalatan™) topically dosed via 2 drops at 15 mcL apart (at a concentration of 50 mcg/mL) for a total dose of 1.5 mcg in one study eye and immediately after received an additional topical dose of 500 mcg of Compound A at 40 mcL formulated in an HPβCD solution in one study eye and vehicle/placebo of HPβCD in saline in the contralateral eye.

Treatment 3
In the third treatment, 10 monkeys received latanoprost (Xalatan™) dosed via 2 drops at 15 mcL apart (at a concentration of 50 mcg/mL) for a total dose of 1.5 mcg in one study eye and 2 drops of saline vehicle in the contralateral eye. This treatment was performed at two separate times with a sufficient washout between treatments. The IOPs of both the study eye and contralateral eye were measured repeatedly using a calibrated pneumotonometer following an application of a topical anesthetic (proparacaine).

Treatment 4
In the fourth treatment, 10 monkeys received latanoprost (Xalatan™) topically dosed via 2 drops at 15 mcL apart (at a concentration of 50 mcg/mL) for a total dose of 1.5 mcg in one study eye and saline in the contralateral eye. Approximately 4 hours later, the monkeys received the additional topical dose of 100 mcg of Compound A at 40 mcL formulated in an aqueous suspension in the same study eye and vehicle/placebo of 0.8% sodium chloride (NaCl), 0.15% citrate, 0.01% benzalkonium chloride, 0.3% polysorbate 80, and 0.7% sodium (Na) carboxymethylcellulose topically in the contralateral eye. The intraocular pressures (IOP) of both the study eye and contralateral eye were measured repeatedly using a calibrated pneumotonometer following an application of a topical anesthetic (proparacaine).

Treatment 5
In the fifth treatment, 10 monkeys received latanoprost (Xalatan™) topically dosed via 2 drops at 15 mcL apart (at a concentration of 50 mcg/mL) for a total dose of 1.5 mcg in one study eye and saline in the contralateral eye. Approximately 5 hours later, the monkeys received the additional topical dose of 100 mcg of Compound A at 40 mcL formulated in an aqueous suspension in the same study eye and vehicle/placebo of 0.8% sodium chloride (NaCl), 0.15% citrate, 0.01% benzalkonium chloride, 0.3% polysorbate 80, and 0.7% sodium (Na) carboxymethylcellulose applied topically in the contralateral eye. The IOPs of both the study eye and contralateral eye were measured repeatedly using a calibrated pneumotonometer following an application of a topical anesthetic (proparacaine).

Figure 2:
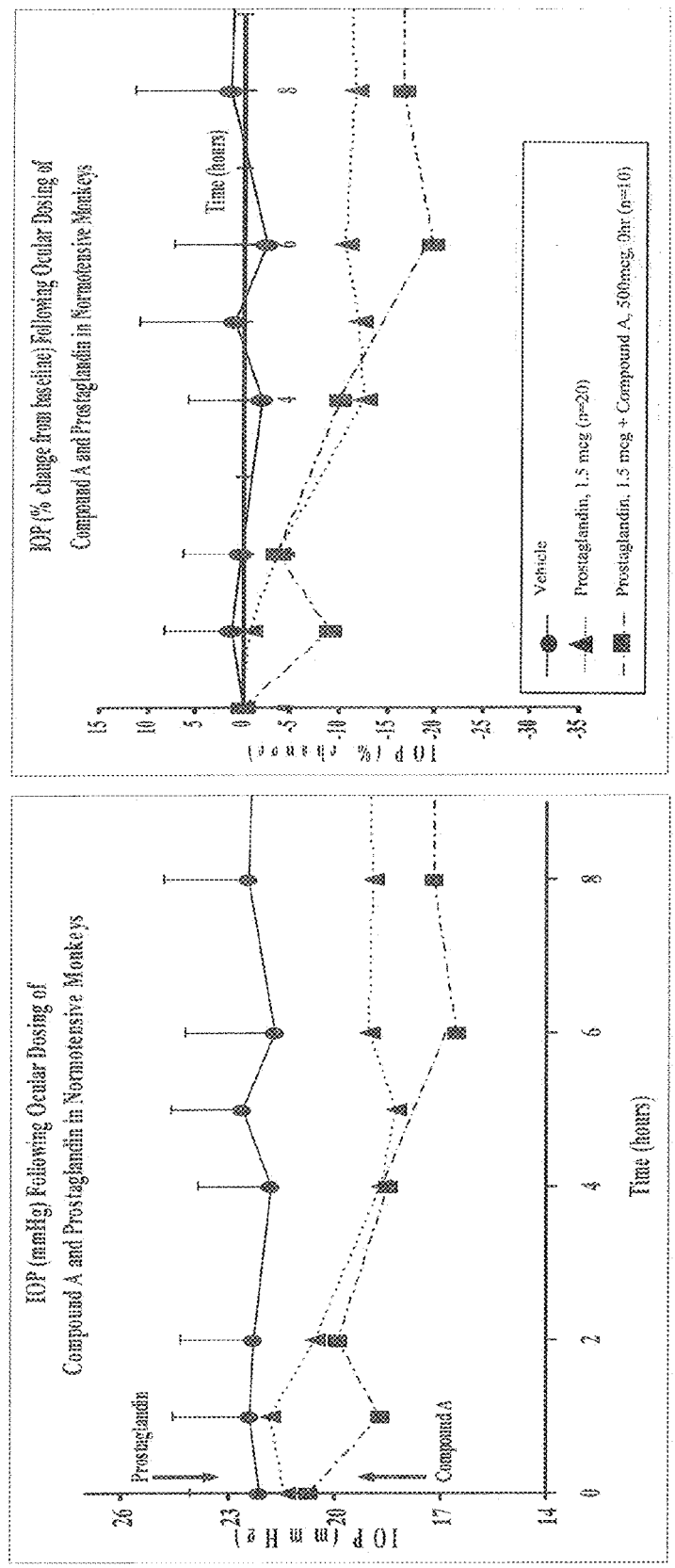
FIG. 2: shows the reduction in IOP (% change from baseline) in normotensive monkeys following ocular dosing of 100 mcg or Compound A at 4 hrs after ocular dosing of a prostaglandin analog compared to the reduction in IOP following dosing of a prostaglandin analog alone.

Results
The results from the treatments are illustrated in FIGS. 1 through 4. The results of Treatment 1 can be seen in FIG. 1, Treatments 2 and 3 in FIG. 2, Treatments 3 and 4 in FIG. 3 and Treatments 3 and 5 in FIG. 4. It can be seen from the plots in FIG. 1 that show the reduction of IOP in (mmHg and % change from baseline) following ocular dosing of 100 mcg of an aqueous suspension of Compound A. The plots in FIG. 2 show the reduction of IOP in (mmHg and % change from baseline) following the simultaneous ocular dosing of 500 mcg of an HPβCD suspension of Compound A and 1.5 mcg of prostaglandin relative to the reduction of IOP seen with the ocular dosing of 1.5 mcg of prostaglandin alone.

Figure 3:
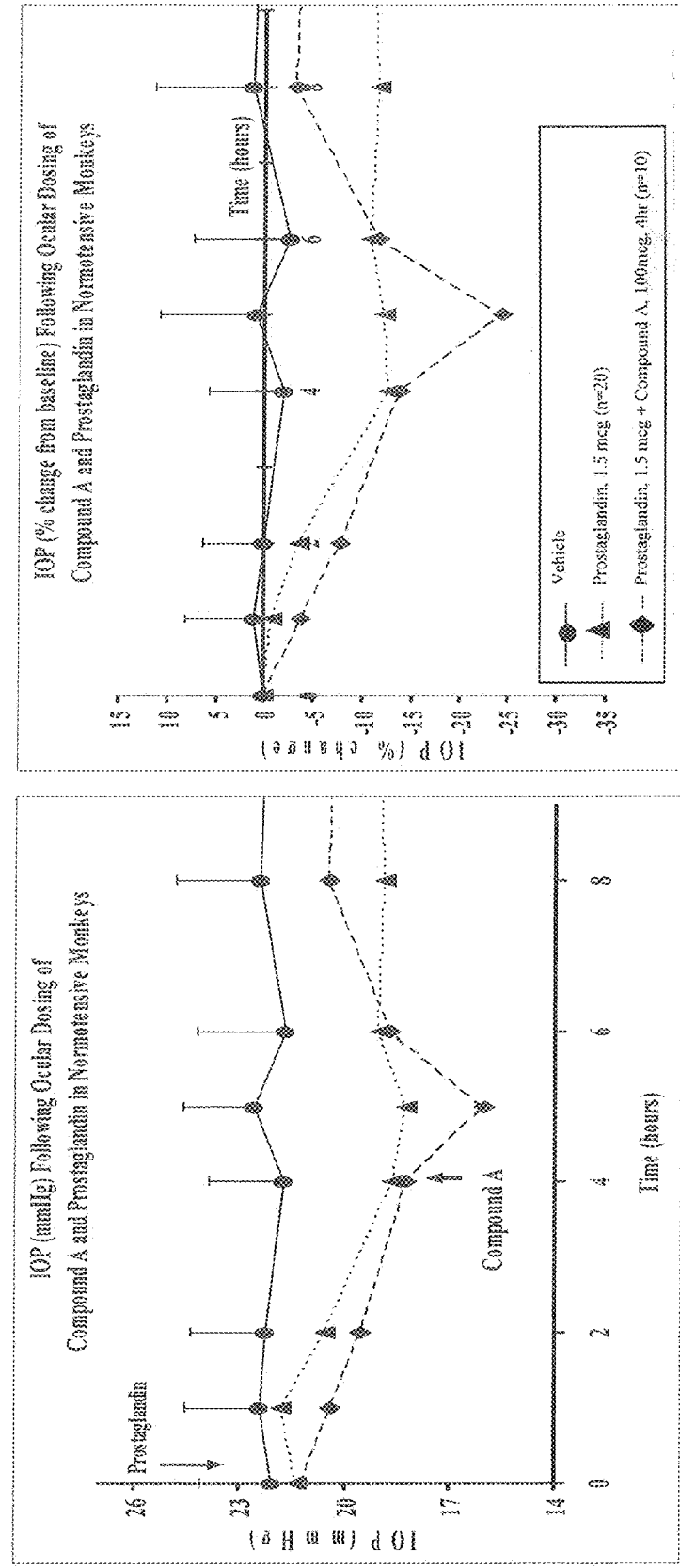
FIG. 3: shows the reduction in IOP (mmHg) in normotensive monkeys following (i) ocular dosing of Compound A at 4 hrs after ocular dosing of a prostaglandin analog compared to the reduction in IOP following dosing of a prostaglandin analog alone and (ii) ocular dosing of 500 mcg Compound A immediately after ocular dosing of a prostaglandin analog compared to the reduction in IOP following dosing of a prostaglandin analog alone
Figure 4:
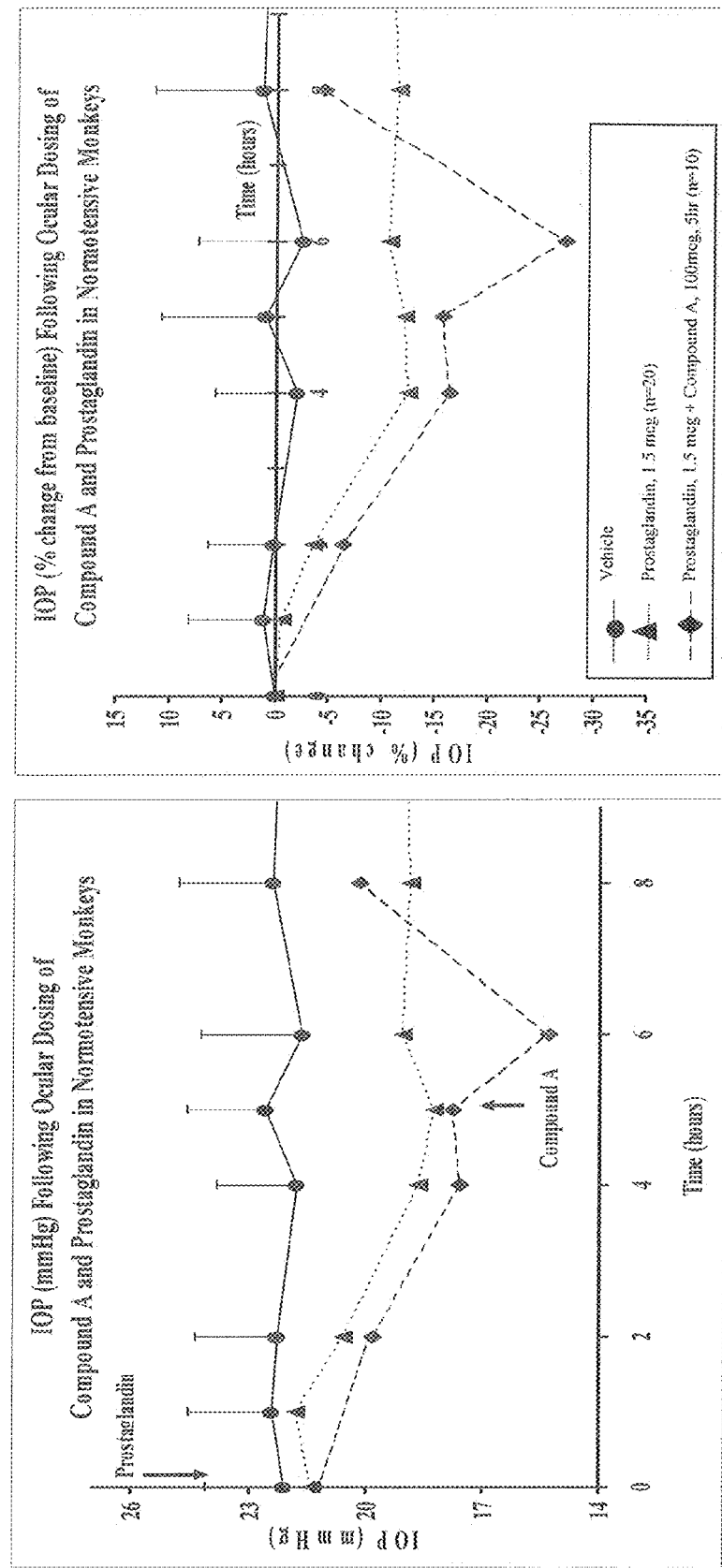
FIG. 4: shows the reduction in IOP (% change from baseline) in normotensive monkeys following (i) ocular dosing of Compound A at 4 hrs after ocular dosing of a prostaglandin analog compared to the reduction in IOP following dosing of a prostaglandin analog alone and (ii) ocular dosing of 500 mcg Compound A immediately after ocular dosing of a prostaglandin analog compared to the reduction in IOP following dosing of a prostaglandin analog alone.

The plots in FIG. 3 show the reduction of IOP in (mmHg and % change from baseline) following the ocular dosing of 100 mcg of an aqueous suspension of Compound A given 4 hours after the ocular dosing of 1.5 mcg of prostaglandin relative to the reduction of IOP seen with ocular dosing of 1.5 mcg of prostaglandin alone. The plots in FIG. 4 show the reduction of IOP in (mmHg and % change from baseline) following the ocular dosing of 100 mcg of an aqueous suspension of Compound A given 5 hours after the ocular dosing of 1.5 mcg of prostaglandin relative to the reduction of IOP seen with ocular dosing of 1.5 mcg of prostaglandin alone. It can be recognized from FIGS. 2 to 4 that two different doses of Compound A were administered and Compound A was also administered simultaneously with latanoprost and subsequent to the administration of latanoprost at two different times. In each arm of the study, a further significant reduction in IOP was observed 1 hour after the administration of Compound A relative to the IOP of the administration of latanoprost alone.

Multidose Study

A multi-dose study was conducted to evaluate the IOP lowering effect of twice-daily topical administration of Compound A in a suspension formulation in combination with once daily topical Latanoprost administration in conscious cynomolgus monkeys. Animals received latanoprost for approximately 2 weeks prior to the combination treatment with Compound A. IOP was routinely monitored beginning prior to the treatment through the combination treatments.

A suspension formulation of 1.625 mg/mL Compound A was formulated in 0.7% sodium carboxymethyl cellulose (CMC), 0.3% polysorbate 80, 0.01% benzalkonium chloride, 0.15% citric acid, and 0.8% sodium chloride (NaCl). The placebo contained these same ingredients, except for Compound A. Latanoprost (0.05 mg/mL) was dosed as supplied commercially. Ten female, ocular normotensive cynomolgus monkeys (*Macaca fascicularis*), aged 3 to 4 years old at initiation of treatment, were acclimated to ocular topical dosing and repeated IOP measurements using a pneumatonometer (Model 30 Classic) without general anesthesia or sedation (conscious) and dosed as indicated in Table 1.

Results

Effect of Repeated Once Daily Topical Administration of Latanoprost on IOP

Figure 5:
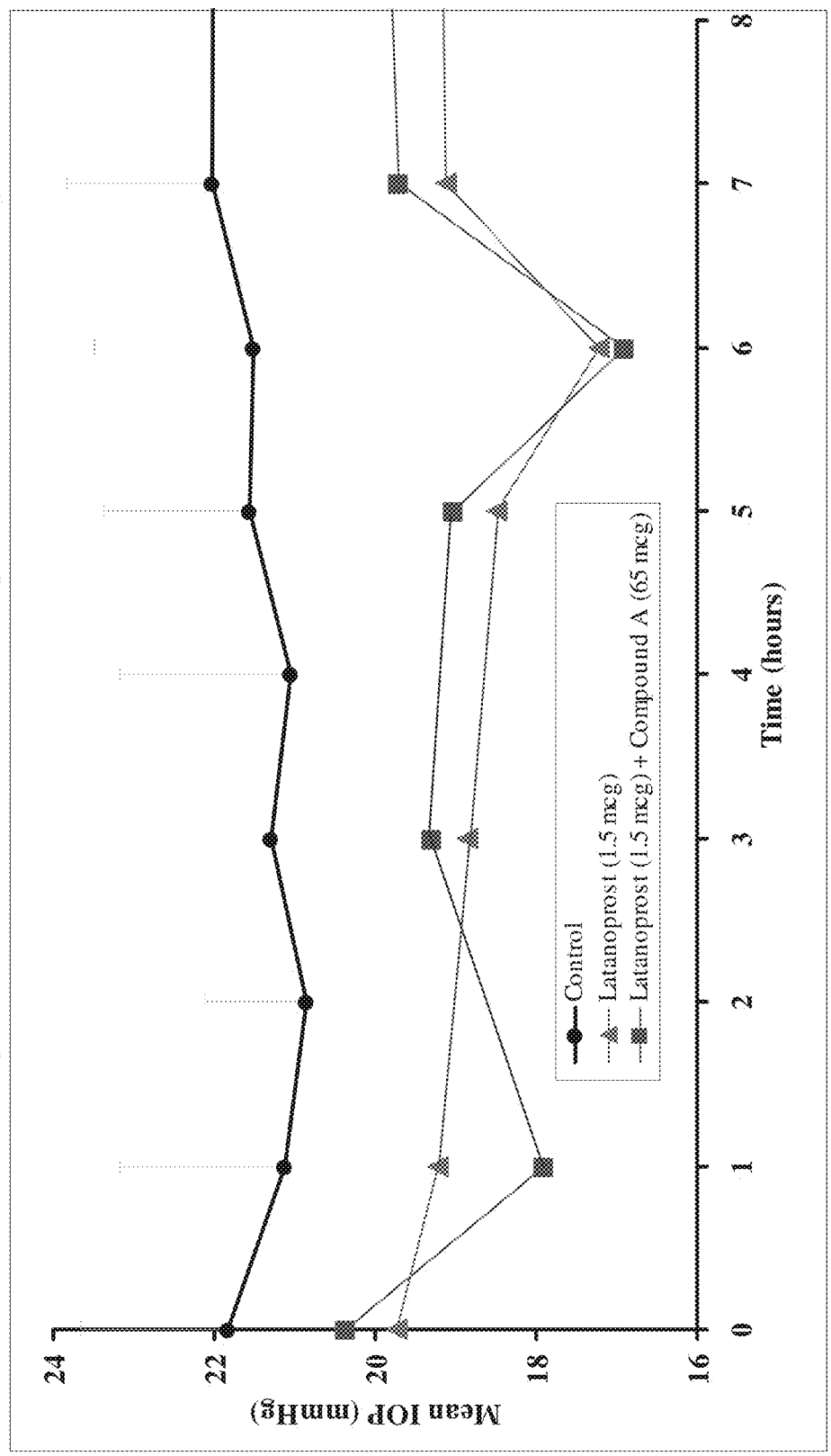
FIG. 5: shows mean IOP (mm Hg) of treated right eye of normotensive monkeys (n=10) after repeated twice daily topical administration of Compound A (65 µg/dose; 130 µg/day) to the right eye following once daily topical dose of Latanoprost (1.5 µg/dose) to the right eye. The combination treatment is compared to the mean IOP following repeated once daily topical administration of Latanoprost (1.5 µg/dose) alone to the right eye. The left eye received controls (balanced salt solution for latanoprost and placebo for Compound A) as the same volume as the right eye. Plots show mean IOP values measured over several days.
Figure 6:
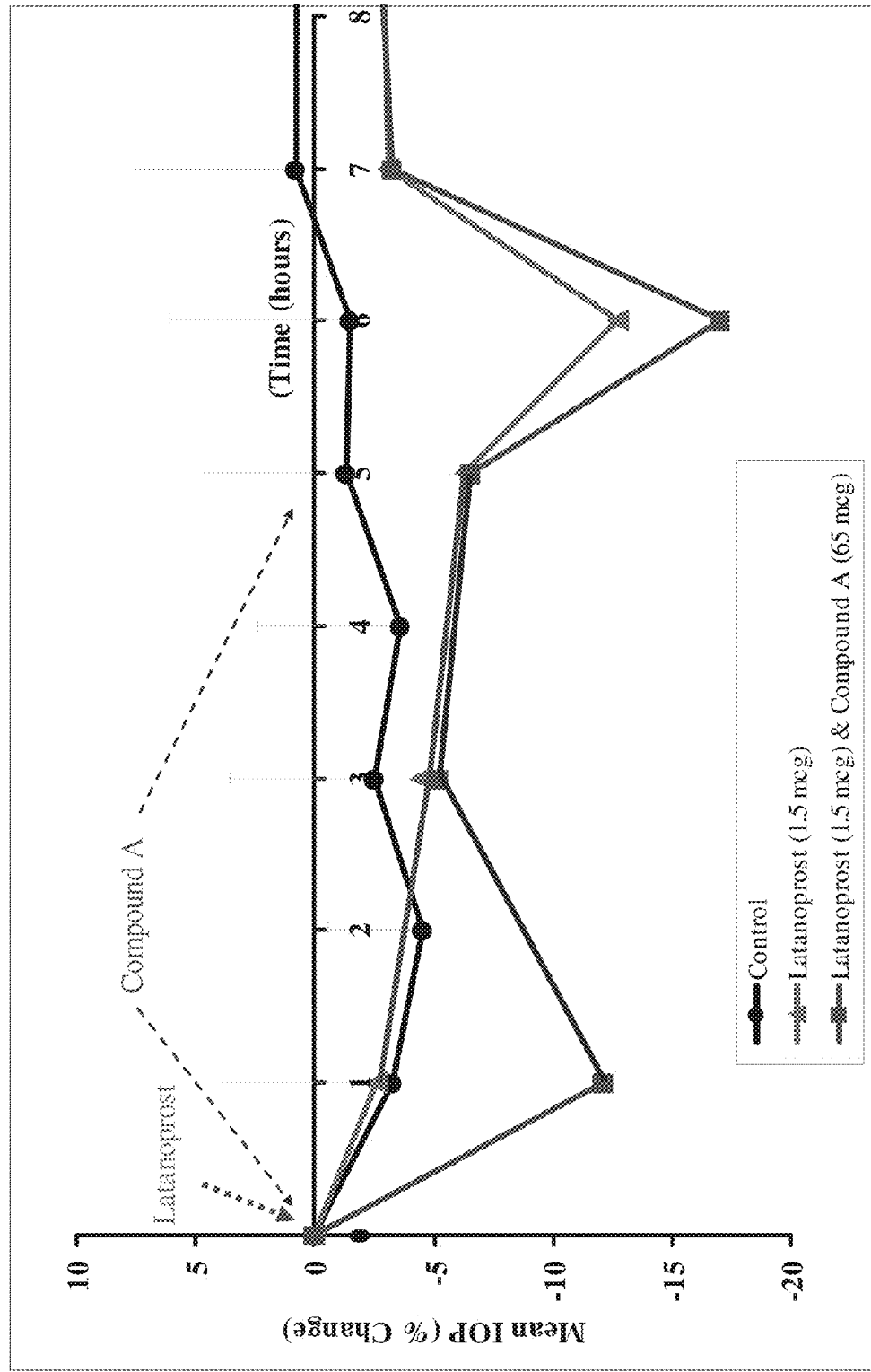
FIG. 6: shows mean percentage change in IOP from baseline of treated right eye of normotensive monkeys (n=10) after twice daily topical administration of Compound A (65 µg/dose; 130 µg/day) to the right eye following once daily topical dose of Latanoprost (1.5 µg/dose) to the right eye. The combination treatment is compared to the mean percentage change in IOP from baseline following repeated once daily topical administration of Latanoprost (1.5 µg/dose) alone to the right eye. The left eye received controls (balanced salt solution for latanoprost and placebo for Compound A) as the same volume as the right eye. Plots show mean percentage change from baseline of IOP measured over several days.

FIG. 5 shows mean IOP (mm Hg) and FIG. 6 shows mean percentage change in IOP from baseline of four separate IOP measurement sessions after repeated once daily topical administration of latanoprost to the right eyes of normotensive monkeys. The mean IOP levels were reduced to about 2 mm Hg at peak trough in the treated eyes. This correlated to approximately 13% reduction from the mean IOP baseline levels. After repeated treatments with latanoprost for two weeks, the IOP of treated eyes was slightly lower than that of the control eyes including at pre-dose times.

Effect of Twice Daily Topical Administration of Compound A in a Suspension Formulation (65 µg Compound A/Dose) in Combination with Once Daily Topical Latanoprost on IOP after Establishment of Steady State IOP Levels with Daily Topical Latanoprost FIG. 5 shows mean IOP (mm Hg) and 6 shows mean percentage change in IOP from baseline of three IOP measurement sessions of treated right eyes in normotensive monkeys following repeated daily topical administration. Compound A (65 µg/dose/eye; 130 µg/eye/day) was delivered twice daily to the right eyes following once daily topical doses of latanoprost (1.5 µg/dose) to the right eyes.

After establishment of steady state IOP levels with daily topical latanoprost for approximately two weeks, the right eye received repeated twice daily treatment of Compound A (65 µg/dose, 130 µg/day) in combination with once daily latanoprost (1.5 µg/eye). The combination treatment showed a greater reduction in IOP compared with that of latanoprost alone at 1 hour after each of the twice daily dose (at Time 0 and 5 hours) of Compound A. Topical administrations of Compound A caused a rapid reduction in IOP compared to the IOP level established by daily topical latanoprost administra-

TABLE 1

Doses and Treatment Regimen

| Duration | Treatment Right Eye[a] | Dose Concentration (mg/mL) | Dose Level Right Eye (µg/dose/eye) | Treatment Left Eye[b] | Dose Level Left Eye | Dose Volume (No. of drops/volume [µL/drop]) |
|---|---|---|---|---|---|---|
| 2 weeks | Latanoprost (QD) | 0.05 | 1.5 | BSS (QD) | 0 | 2/15 |
| 1 week | Latanoprost (QD) | 0.05 | 1.5 | BSS (QD) | 0 | 2/15 |
|  | Compound A Suspension Formulation (BID) | 1.625 | 65 | Placebo Control (bid) | 0 | 1/40 |

QD = Once each day.
BID = Twice each day.
BSS = Balanced salt solution.
[a]For the right eyes, Latanoprost was dosed once daily starting approximately 2 weeks prior to the combination treatment; the drug was administered via two drops (1.5 µg) approximately 1 minute apart. For the combination, Compound A was dosed as a single drop at 65 µg/dose BID (for a total dose of 130 µg/day) approximately 5 hours apart.
[b]For the left eyes, respective matching controls, balanced salt solution (BSS) for latanoprost and Placebo for Compound A. The volumes and regimen were similar to that of treated right eyes.

Intraocular pressure was measured from both eyes (three readings/eye/time interval with mean values represented in the data tables) beginning approximately 1 hour predose, at Time 0 (just prior to dosing), and after dosing at various time intervals. Mean IOP values and the percent change in IOP levels from the baseline level were calculated. The FIGS. 5 and 6 show summarized data from this phase of the study of the combined IOP mean values of treatments and standard deviation of the mean for the control. The control plot includes the combined mean values of all treatments (BSS alone and BSS in combination with Placebo). The mean IOP levels in the control eye ranged from 21 to 22 mmHg.

tion. IOP was reduced to a greater extent with the combination treatment than that observed with latanoprost alone. At peak troughs, IOP was reduced to approximately 12% and 17% after the first and second daily doses, respectively. This trend was consistent in each IOP session of the combination treatment.

It is anticipated that results of a similar or more significant extent would be observed with further pre-clinical studies in hypertensive monkeys and would similarly extend to other mammals including humans.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to combinations, kits, compounds, means, methods, and/or steps disclosed herein.

We claim:

1. A pharmaceutical composition comprising a combination comprising i) an adenosine receptor $A_1$ agonist formulated with a pharmaceutically acceptable carrier and ii) a prostaglandin analog formulated with a pharmaceutically effective carrier, wherein the adenosine receptor $A_1$ agonist is a compound of Formula (I)

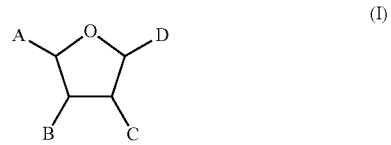

(I)

or a pharmaceutically acceptable salt thereof,
wherein
A is —$CH_2OH$, —$CH_2ONO_2$ or —$CH_2OSO_3H$;
B and C are —OH;
D is

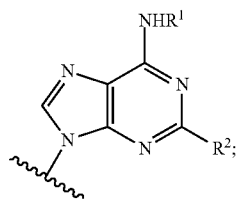

A and B are trans with respect to each other;
B and C are cis with respect to each other;
C and D are cis or trans with respect to each other;
$R^1$ is —H, —$C_1$-$C_{10}$ alkyl, -aryl, -3- to 7-membered monocyclic heterocyclyl, -8- to 12-membered bicyclic heterocyclyl, —$C_3$-$C_8$ monocyclic cycloalkyl, —$C_3$-$C_8$ monocyclic cycloalkenyl, —$C_8$-$C_{12}$ bicyclic cycloalkyl, —$C_8$-$C_{12}$ bicyclic cycloalkenyl —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), or —$(CH_2)_n$-aryl;
$R^2$ is —H, halo, —CN, —$NHR^4$, —$NHC(O)R^4$, —$NHC(O)OR^4$, —$NHC(O)NHR^4$,—$NHNHC(O)R^4$, —$NHNHC(O)OR^4$, —$NHNHC(O)NHR^4$, or —NH—N=$C(R^6)R^7$;
$R^4$ is —$C_1$-$C_{15}$ alkyl, -aryl, —$(CH_2)_n$-aryl, —$(CH_2)_n$-(3- to 7-membered monocyclic heterocyclyl), —$(CH_2)_n$-(8- to 12-membered bicyclic heterocyclyl), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —C≡C—($C_1$-$C_{10}$ alkyl) or —C≡C-aryl;
$R^6$ is —$C_1$-$C_{10}$ alkyl, -aryl, —$(CH_2)_n$-aryl, —$(CH_2)_n$-(3- to 7-membered monocyclic heterocyclyl), —$(CH_2)_n$-(8- to 12-membered bicyclic heterocyclyl), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$—($C_3$-$C_8$ monocyclic cycloalkenyl), -phenylene-$(CH_2)_n$COOH, or -phenylene-$(CH_2)_n$COO—($C_1$-$C_{10}$ alkyl);
$R^7$ is —H, —$C_1$-$C_{10}$ alkyl, -aryl, —$(CH_2)_n$-aryl, —$(CH_2)_n$-(3- to 7-membered monocyclic heterocyclyl), —$(CH_2)_n$-(8- to 12-membered bicyclic heterocyclyl), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkenyl) or —$(CH_2)_n$—($C_8$-$C_{12}$ bicyclic cycloalkyl) and each n is independently an integer ranging from 1 to 5.

2. The composition of claim 1, wherein the prostaglandin analog is selected from the group consisting of latanoprost, travoprost, unoprostone and bimatoprost.

3. The composition of claim 1, wherein the compound of Formula (I) is selected from the group consisting of:

Compound A

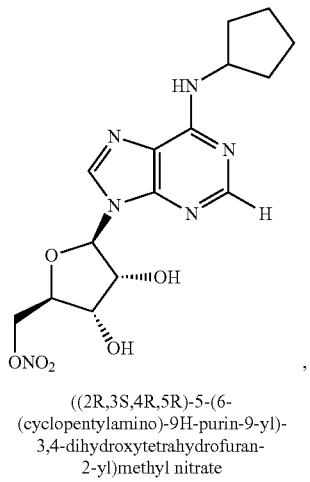

((2R,3S,4R,5R)-5-(6-(cyclopentylamino)-9H-purin-9-yl)-3,4-dihydroxytetrahydrofuran-2-yl)methyl nitrate Compound B

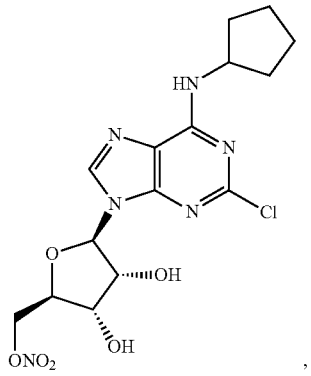

((2R,3S,4R,5R)-5-(2-chloro-6-(cyclopentylamino)-9H-purin-9-yl)-3,4-dihydroxytetrahydrofuran-2-yl)methyl nitrate Compound C

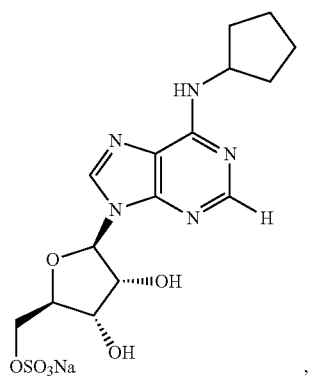

sodium ((2R,3S,4R,5R)-5-
(6-(cyclopentylamino)-
9H-purin-9-yl)-3,4-
dihydroxytetrahydrofuran-
2-yl)methyl sulfate Compound D

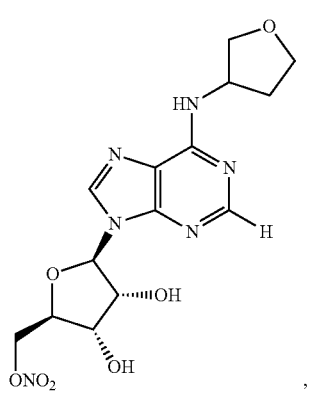

((2R,3S,4R,5R)-3,4-dihydroxy-5-
(6-(tetrahydrofuran-3-ylamino)-9H-
purin-9-yl)tetrahydrofuran-2-yl)
methyl nitrate Compound E

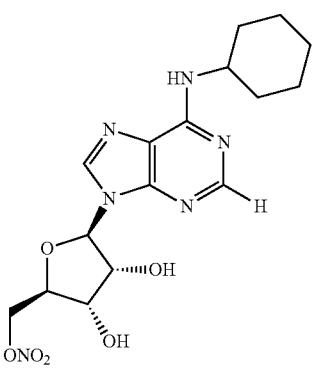

((2R,3S,4R,5R)-5-(6-
(cyclohexylamino)-9H-purin-9-yl)-
3,4-dihydroxytetrahydrofuran-2-yl)
methyl nitrate Compound F

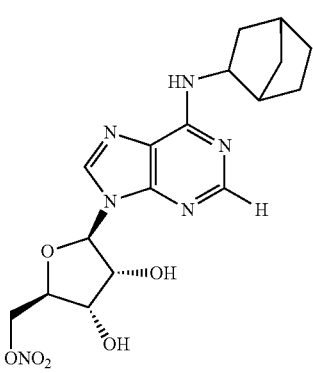

((2R,3S,4R,5R)-5-(6-(bicycle)-[2.2.1]-
heptan-2-ylamino-9H-purin-9-yl)-
3,4-dihydroxytetrahydrofuran-2-yl)
methyl nitrate Compound G

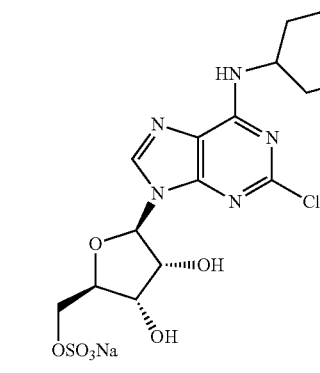

sodium ((2R,3S,4R,5R)-5-(2-chloro-6-
(cyclohexylamino)-9H-purin-9-yl)-
3,4-dihydroxytetrahydrofuran-2-yl)
methyl sulfate Compound H

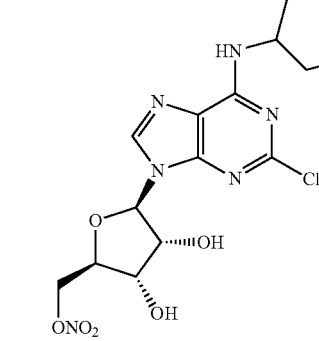

((2R,3S,4R,5R)-5-(2-chloro-6-
(cyclohexylamino)-9H-purin-9-yl)-
3,4-dihydroxytetrahydrofuran-2-yl)
methyl nitrate -continued

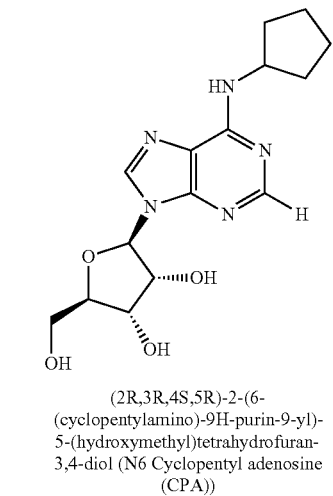

(2R,3R,4S,5R)-2-(6-
(cyclopentylamino)-9H-purin-9-yl)-
5-(hydroxymethyl)tetrahydrofuran-
3,4-diol (N6 Cyclopentyl adenosine
(CPA))

Compound J

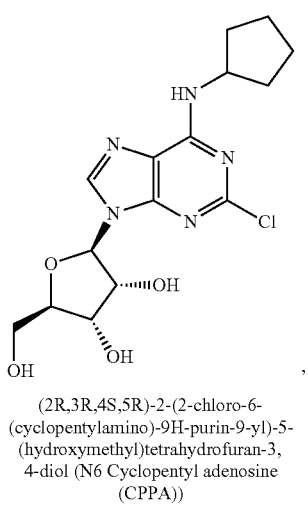

(2R,3R,4S,5R)-2-(2-chloro-6-
(cyclopentylamino)-9H-purin-9-yl)-5-
(hydroxymethyl)tetrahydrofuran-3,
4-diol (N6 Cyclopentyl adenosine
(CPPA))

and pharmaceutically acceptable salts thereof.

4. The composition of claim 1, wherein the adenosine receptor $A_1$ agonist is Compound A, ((2R,3S,4R,5R)-5-(6-(cyclopentylamino)-9H-purin-9-yl)-3,4-dihydroxytetrahydrofuran-2-yl)methyl nitrate or a pharmaceutically acceptable salt thereof.

5. The composition of claim 1, wherein the $A_1$ agonist and prostaglandin analog are provided in separate unit dosage forms.

6. The composition of claim 1, wherein the $A_1$ agonist is provided in a dosage of about 0.05 mg/ml to about 7.0 mg/ml and the prostaglandin analog is provided in a dosage of about 30 μg/ml to about 50 μg/ml.

7. The composition of claim 6, wherein the $A_1$ agonist is provided in a dosage of about 20-700 μg.

8. The composition of claim 6, wherein the $A_1$ agonist is provided in a dosage of about 20-350 μg.

9. The composition of claim 1, wherein the $A_1$ agonist and the prostaglandin analog are formulated for topical administration.

10. The composition of any one of claims 5-9, wherein the A1 agonist is compound A, ((2R,3S,4R,5R)5-(6-(cyclopendtylamino-9H-purin-9-yl)-3,4-dihydroxytetrahydrofuran-2yl)methyl nitrate or pharmaceutically acceptable salt thereof.

11. A kit comprising i) an adenosine receptor $A_1$ agonist and ii) a prostaglandin analog, wherein the adenosine receptor $A_1$ agonist is a compound of Formula (I)

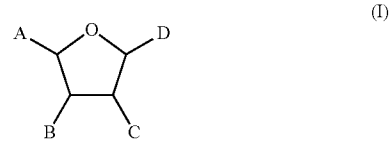

or a pharmaceutically acceptable salt thereof,
wherein
A is —CH$_2$OH, —CH$_2$ONO$_2$ or —CH$_2$OSO$_3$H;
B and C are —OH;
D is

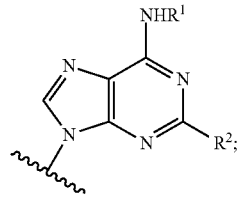

A and B are trans with respect to each other;
B and C are cis with respect to each other;
C and D are cis or trans with respect to each other;
R$^1$ is —H, —C$_1$-C$_{10}$ alkyl, -aryl, -3- to 7-membered monocyclic heterocyclyl, -8- to 12-membered bicyclic heterocyclyl, —C$_3$-C$_8$ monocyclic cycloalkyl, —C$_3$-C$_8$ monocyclic cycloalkenyl, —C$_8$-C$_{12}$ bicyclic cycloalkyl, —C$_8$—C$_{12}$ bicyclic cycloalkenyl-(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), or —(CH$_2$)$_n$-aryl;
R$^2$ is —H, halo, —CN, —NHR$^4$, —NHC(O)R$^4$, —NHC(O)OR$^4$, —NHC(O)NHR$^4$, —NHNHC(O)R$^4$, —NHNHC(O)OR$^4$, —NHNHC(O)NHR$^4$, or —NH—N═C(R$^6$)R$^7$;
R$^4$ is —C$_1$-C$_{15}$ alkyl, -aryl, —(CH$_2$)$_n$-aryl, —(CH$_2$)$_n$-(3- to 7-membered monocyclic heterocyclyl), —(CH$_2$)$_n$-(8- to 12-membered bicyclic heterocyclyl), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;
R$^6$ is —C$_1$-C$_{10}$ alkyl, -aryl, —(CH$_2$)$_n$-aryl, —(CH$_2$)$_n$-(3- to 7-membered monocyclic heterocyclyl), —(CH$_2$)$_n$-(8- to 12-membered bicyclic heterocyclyl), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$—(C$_3$-C$_8$ monocyclic cycloalkenyl), -phenylene-(CH$_2$)$_n$COOH, or -phenylene-(CH$_2$)$_n$COO—(C$_1$-C$_{10}$ alkyl);
R$^7$ is —H, —C$_1$-C$_{10}$ alkyl, -aryl, —(CH$_2$)$_n$-aryl, —(CH$_2$)$_n$-(3- to 7-membered monocyclic heterocyclyl), —(CH$_2$)$_n$-(8- to 12-membered bicyclic heterocyclyl), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkenyl) or —(CH$_2$)$_n$—(C$_8$-C$_{12}$ bicyclic cycloalkyl) and each n is independently an integer ranging from 1 to 5.

12. The kit of claim 11, wherein the prostaglandin analog is selected from the group consisting of latanoprost, travoprost, unoprostone and bimatoprost.

13. The kit of claim 11, wherein the compound of Formula (I) is selected from the group consisting of:

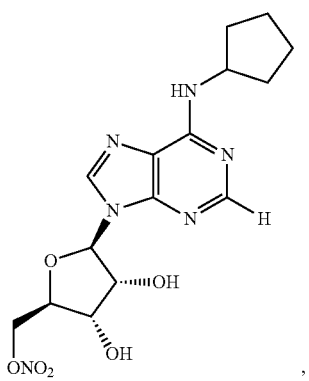

Compound A ((2R,3S,4R,5R)-5-(6-
(cyclopentylamino)-9H-purin-9-yl)-
3,4-dihydroxytetrahydrofuran-
2-yl)methyl nitrate

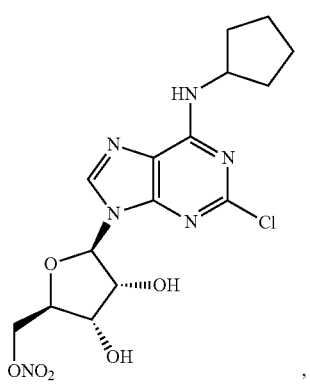

Compound B ((2R,3S,4R,5R)-5-(2-
chloro-6-(cyclopentylamino)-
9H-purin-9-yl)-3,4-
dihydroxytetrahydrofuran-
2-yl)methyl nitrate

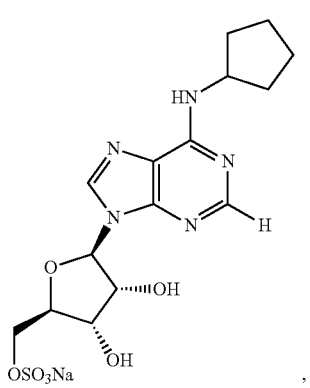

Compound C sodium ((2R,3S,4R,5R)-5-
(6-(cyclopentylamino)-
9H-purin-9-yl)-3,4-
dihydroxytetrahydrofuran-
2-yl)methyl sulfate -continued

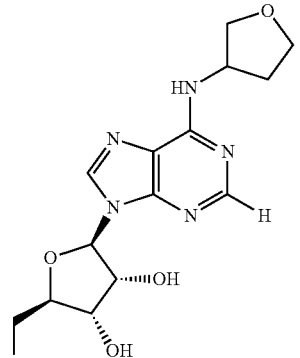

Compound D ((2R,3S,4R,5R)-3,4-dihydroxy-5-
(6-(tetrahydrofuran-3-ylamino)-9H-
purin-9-yl)tetrahydrofuran-2-yl)
methyl nitrate

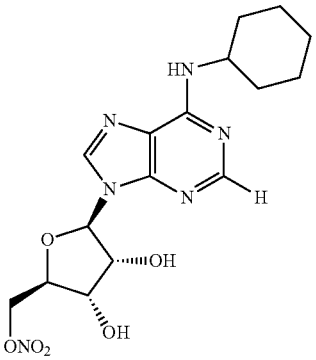

Compound E ((2R,3S,4R,5R)-5-(6-
(cyclohexylamino)-9H-purin-9-yl)-
3,4-dihydroxytetrahydrofuran-2-yl)
methyl nitrate

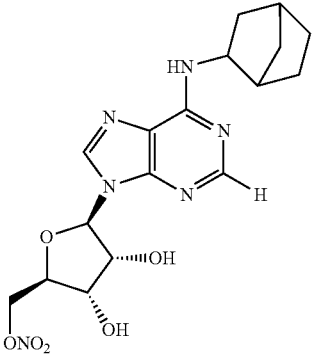

Compound F ((2R,3S,4R,5R)-5-(6-(bicycle)-[2.2.1]-
heptan-2-ylamino-9H-purin-9-yl)-
3,4-dihydroxytetrahydrofuran-2-yl)
methyl nitrate -continued Compound G

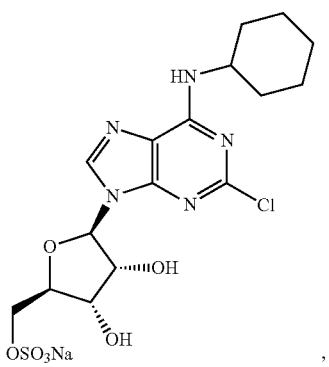

sodium ((2R,3S,4R,5R)-5-(2-chloro-6-
(cyclohexylamino)-9H-purin-9-yl)-
3,4-dihydroxytetrahydrofuran-2-yl)
methyl sulfate Compound H

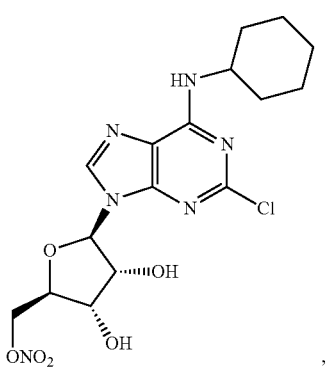

((2R,3S,4R,5R)-5-(2-chloro-6-
(cyclohexylamino)-9H-purin-9-yl)-
3,4-dihydroxytetrahydrofuran-2-yl)
methyl nitrate Compound I

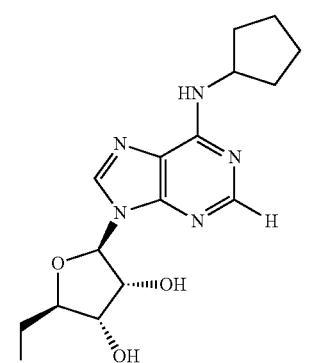

(2R,3R,4S,5R)-2-(6-
(cyclopentylamino)-9H-purin-9-yl)-
5-(hydroxymethyl)tetrahydrofuran-
3,4-diol (N6 Cyclopentyl adenosine
(CPA))

-continued

Compound J

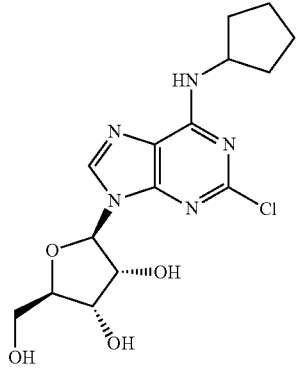

(2R,3R,4S,5R)-2-(2-chloro-6-
(cyclopentylamino)-9H-purin-9-yl)-5-
(hydroxymethyl)tetrahydrofuran-3,
4-diol (N6 Cyclopentyl adenosine
(CPPA))

and pharmaceutically acceptable salts thereof.

14. The kit of claim 11, wherein the $A_1$ agonist is provided in a dosage of about 0.05 mg/ml to about 7.0 mg/ml and the prostaglandin analog is provided in a dosage of about 30 μg/ml to about 50 μg/ml.

15. the kit of claim 14, wherein the $A_1$ agonist is provided in a dosage of about 20-700μg.

16. The kit of claim 14, wherein the $A_1$ agonist is provided in a dosage of the about 20-350 μg.

17. The composition of any one of claims 11 and 14-16, wherein the A1 agonist is compound A, (2R,3S,4R,5R)-5-(6-(cyclopentylamino)-9H-purin-9-yl)-3,4-dihydroxytetrahydrofuran-2-yl) methyl nitrate or a pharmaceutically acceptable salt thereof.

18. A method of reducing intraocular pressure (IOP) and associated diseases and conditions caused by elevated IOP in a subject in need thereof by administering to an affected eye of the subject, an effective amount of:
(i) an adenosine receptor $A_1$ agonist compound of Formula (I)

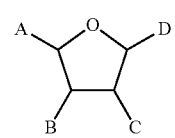
(I)

or a pharmaceutically acceptable salt thereof,
wherein
A is —$CH_2OH$, —$CH_2ONO_2$ or —$CH_2OSO_3H$;
B and C are —OH;
D is

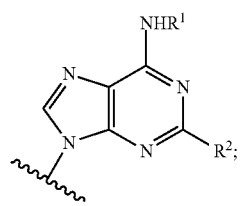

A and B are trans with respect to each other;

B and C are cis with respect to each other;

C and D are cis or trans with respect to each other;

$R^1$ is —H, —$C_1$-$C_{10}$ alkyl, -aryl, -3- to 7-membered monocyclic heterocyclyl, -8- to 12-membered bicyclic heterocyclyl, —$C_3$-$C_8$ monocyclic cycloalkyl, —$C_3$-$C_8$ monocyclic cycloalkenyl, —$C_8$-$C_{12}$ bicyclic cycloalkyl, —$C_8$-$C_{12}$ bicyclic cycloalkenyl —($CH_2$)$_n$—($C_3$-$C_8$ monocyclic cycloalkyl), —($CH_2$)$_n$—($C_3$-$C_8$ monocyclic cycloalkenyl), —($CH_2$)$_n$—($C_8$-$C_{12}$ bicyclic cycloalkyl), —($CH_2$)$_n$—($C_8$-$C_{12}$ bicyclic cycloalkenyl), or —($CH_2$)$_n$-aryl;

$R^2$ is —H, halo, —CN, —$NHR^4$, —NHC(O)$R^4$, —NHC(O)O$R^4$, —NHC(O)NH$R^4$, —NHNHC(O)$R^4$, —NHNHC(O)O$R^4$, —NHNHC(O)NH$R^4$, or —NH—N═C($R^6$)$R^7$;

$R^4$ is —$C_1$-$C_{15}$ alkyl, -aryl, —($CH_2$)$_n$-aryl, —($CH_2$)$_n$-(3- to 7-membered monocyclic heterocyclyl), —($CH_2$)$_n$-(8- to 12-membered bicyclic heterocyclyl), —($CH_2$)$_n$—($C_3$-$C_8$ monocyclic cycloalkyl), —($CH_2$)$_n$—($C_3$-$C_8$ monocyclic cycloalkenyl), —($CH_2$)$_n$—($C_8$-$C_{12}$ bicyclic cycloalkyl), —($CH_2$)$_n$—($C_8$-$C_{12}$ bicyclic cycloalkenyl), —C≡C—($C_1$-$C_{10}$ alkyl) or —C≡C-aryl;

$R^6$ is —$C_1$-$C_{10}$ alkyl, -aryl, —($CH_2$)$_n$-aryl, —($CH_2$)$_n$-(3- to 7-membered monocyclic heterocyclyl), —($CH_2$)$_n$-(8- to 12-membered bicyclic heterocyclyl), —($CH_2$)$_n$—($C_3$-$C_8$ monocyclic cycloalkyl), —($CH_2$)$_n$—($C_3$-$C_8$ monocyclic cycloalkenyl), —($CH_2$)$_n$—($C_8$-$C_{12}$ bicyclic cycloalkyl), —($CH_2$)$_n$—($C_8$-$C_{12}$ bicyclic cycloalkenyl), —($CH_2$)$_n$—($C_3$-$C_8$ monocyclic cycloalkenyl), -phenylene-($CH_2$)$_n$COOH, or -phenylene-($CH_2$)$_n$COO—($C_1$-$C_{10}$ alkyl);

$R^7$ is —H, —$C_1$-$C_{10}$ alkyl, -aryl, —($CH_2$)$_n$-aryl, —($CH_2$)$_n$-(3- to 7-membered monocyclic heterocyclyl), —($CH_2$)$_n$-(8- to 12-membered bicyclic heterocyclyl), —($CH_2$)$_n$—($C_3$-$C_8$ monocyclic cycloalkyl), —($CH_2$)$_n$—($C_3$-$C_8$ monocyclic cycloalkenyl), —($CH_2$)$_n$—($C_8$-$C_{12}$ bicyclic cycloalkenyl) or —($CH_2$)$_n$—($C_8$-$C_{12}$ bicyclic cycloalkyl) and each n is independently an integer ranging from 1 to 5, and (ii) a prostaglandin analog.

19. The method of claim 18, wherein the diseases and conditions caused by elevated IOP in a human are selected from the group consisting of normal-tension glaucoma, ocular hypertension (OHT), and primary open-angle glaucoma (POAG).

20. The method of claim 18, wherein the $A_1$ receptor agonist compound is applied to an eye of the subject in need thereof, simultaneously, separately or sequentially to the application of the prostaglandin analog to the eye of the subject.

21. The method of claim 20, wherein the $A_1$ receptor agonist compound is applied to an eye of the subject in need thereof, simultaneously to the application of the prostaglandin analog to the eye of the subject.

22. The method of claim 20, wherein the $A_1$ receptor agonist compound is applied to an eye of the subject in need thereof, sequentially to the application of the prostaglandin analog to the eye of the subject.

23. The method of claim 18, wherein the compound of Formula (I) is selected from the group consisting of:

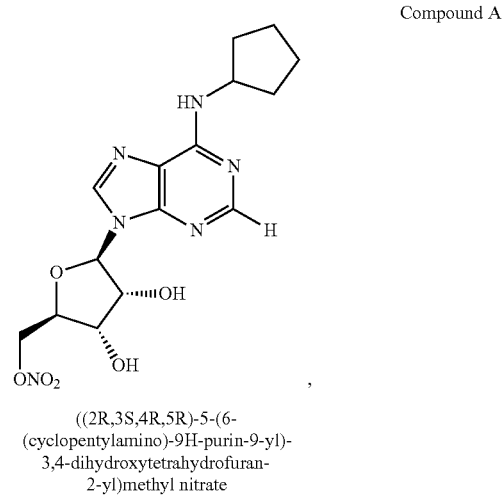

Compound A ((2R,3S,4R,5R)-5-(6-(cyclopentylamino)-9H-purin-9-yl)-3,4-dihydroxytetrahydrofuran-2-yl)methyl nitrate

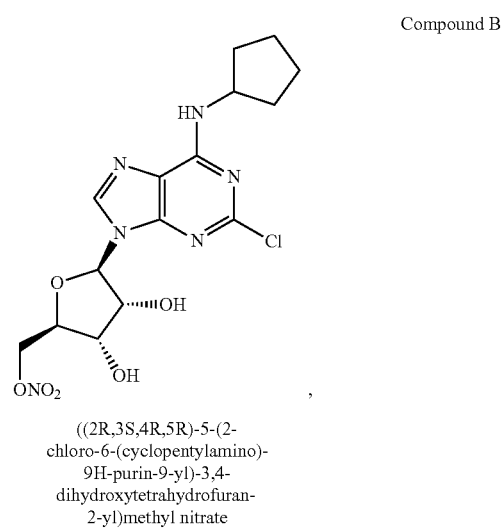

Compound B ((2R,3S,4R,5R)-5-(2-chloro-6-(cyclopentylamino)-9H-purin-9-yl)-3,4-dihydroxytetrahydrofuran-2-yl)methyl nitrate

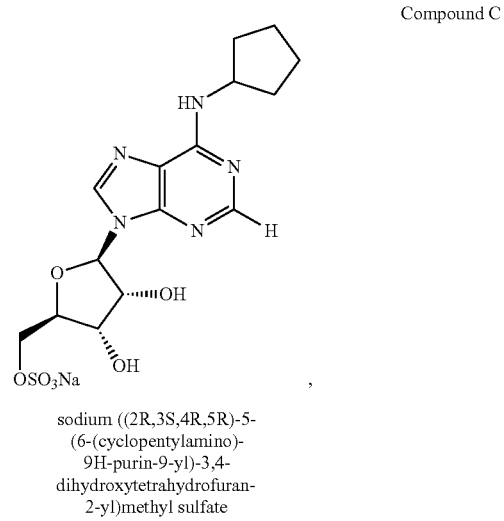

Compound C sodium ((2R,3S,4R,5R)-5-(6-(cyclopentylamino)-9H-purin-9-yl)-3,4-dihydroxytetrahydrofuran-2-yl)methyl sulfate -continued Compound D

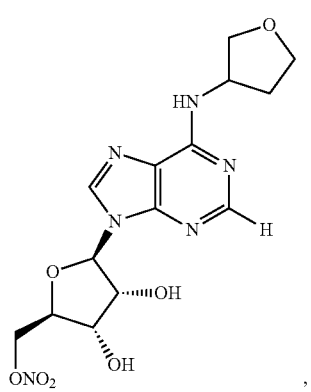

((2R,3S,4R,5R)-3,4-dihydroxy-5-
(6-(tetrahydrofuran-3-ylamino)-9H-
purin-9-yl)tetrahydrofuran-2-yl)
methyl nitrate Compound E

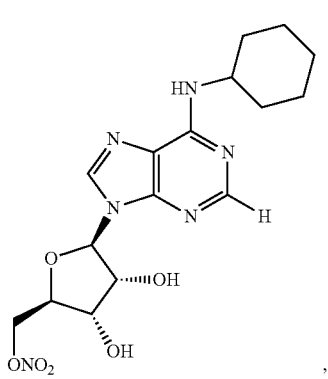

((2R,3S,4R,5R)-5-(6-
(cyclohexylamino)-9H-purin-9-yl)-
3,4-dihydroxytetrahydrofuran-2-yl)
methyl nitrate Compound F

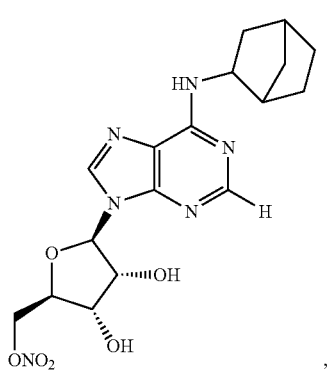

((2R,3S,4R,5R)-5-(6-(bicycle)-[2.2.1]-
heptan-2-ylamino-9H-purin-9-yl)-
3,4-dihydroxytetrahydrofuran-2-yl)
methyl nitrate -continued Compound G

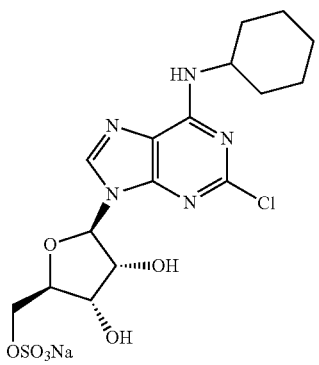

sodium ((2R,3S,4R,5R)-5-(2-chloro-6-
(cyclohexylamino)-9H-purin-9-yl)-
3,4-dihydroxytetrahydrofuran-2-yl)
methyl sulfate Compound H

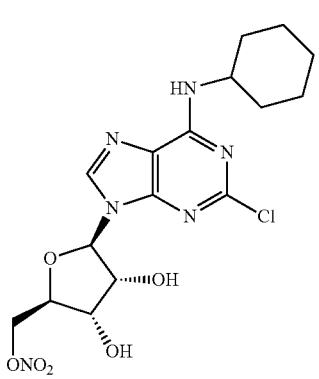

((2R,3S,4R,5R)-5-(2-chloro-6-
(cyclohexylamino)-9H-purin-9-yl)-
3,4-dihydroxytetrahydrofuran-2-yl)
methyl nitrate Compound I

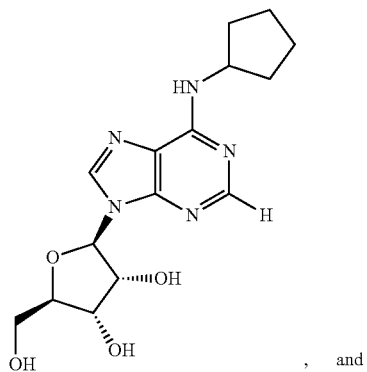

, and (2R,3R,4S,5R)-2-(6-
(cyclopentylamino)-9H-purin-9-yl)-
5-(hydroxymethyl)tetrahydrofuran-
3,4-diol (N6 Cyclopentyl adenosine
(CPA))

-continued

Compound J

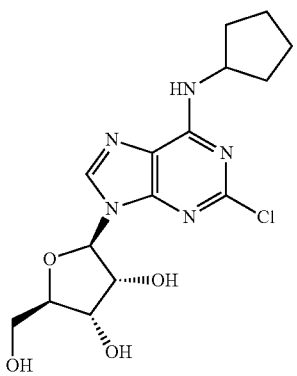

(2R,3R,4S,5R)-2-(2-chloro-6-(cyclopentylamino)-9H-purin-9-yl)-5-(hydroxymethyl)tetrahydrofuran-3,4-diol ($N^6$ Cyclopentyl adenosine (CPPA))

or pharmaceutically acceptable salts thereof.

24. The method of claim 18, wherein the $A_1$ receptor agonist compound is compound A ((2R,3S,4R,5R)-5-(6-(cyclopentylamino)-9H-purin-9-yl)-3,4-dihydroxytetrahydrofuran-2-yl)methyl nitrate.

25. The method of claim 18, wherein $A_1$ receptor agonist compound and the prostaglandin analog are administered topically to an eye of the subject.

* * * * *